United States Patent
Okada et al.

(10) Patent No.: US 8,986,197 B2
(45) Date of Patent: Mar. 24, 2015

(54) MEDICAL SYSTEM AND ENDOSCOPE SYSTEM

(75) Inventors: Tsutomu Okada, Tachikawa (JP); Hiroaki Ichikawa, Hachioji (JP); Takaaki Komiya, Akiruno (JP); Yoshio Onuki, Hachioji (JP); Kazuki Honda, Hachioji (JP); Yasuhito Kura, Hachioji (JP); Kazushi Murakami, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 1318 days.

(21) Appl. No.: 11/708,622

(22) Filed: Feb. 20, 2007

(65) Prior Publication Data

US 2008/0200756 A1 Aug. 21, 2008

(51) Int. Cl.
| | |
|---|---|
| *A61B 1/00* | (2006.01) |
| *A61B 1/04* | (2006.01) |
| *A61B 17/00* | (2006.01) |
| *A61B 17/10* | (2006.01) |
| *A61B 1/018* | (2006.01) |

(52) U.S. Cl.
CPC .............. *A61B 1/018* (2013.01); *A61B 1/00133* (2013.01); *A61B 2017/00398* (2013.01)
USPC ............... 600/106; 600/104; 600/114; 606/1; 606/139

(58) Field of Classification Search
CPC ........... A61B 1/00131; A61B 1/00133; A61B 1/00137; A61B 1/0014; A61B 1/00087; A61B 1/0016; A61B 1/012; A61B 1/018
USPC ................. 600/101, 114, 118, 121, 123–125, 600/104–107; 604/156, 198, 510, 528; 606/1, 205–209, 139–150
See application file for complete search history.

(56) References Cited

U.S. PATENT DOCUMENTS

| | | | |
|---|---|---|---|
| 4,721,116 A * | 1/1988 | Schintgen et al. ............ 600/564 |
| 5,346,498 A * | 9/1994 | Greelis et al. ................. 606/108 |
| 5,695,491 A | 12/1997 | Silverstein |
| 6,726,675 B1 | 4/2004 | Beyar |
| 2004/0133228 A1* | 7/2004 | Bayer ........................... 606/190 |
| 2005/0250989 A1 | 11/2005 | Suzuki |
| 2005/0256562 A1 | 11/2005 | Clerc et al. |

FOREIGN PATENT DOCUMENTS

| | | |
|---|---|---|
| EP | 1 568 306 A1 | 8/2005 |
| JP | 08-126648 | 5/1996 |

(Continued)

OTHER PUBLICATIONS

Japanese Office Action dated Nov. 13, 2012 issued in Japanese Patent Application No. 2008-033563.

*Primary Examiner* — Ryan Henderson
(74) *Attorney, Agent, or Firm* — Scully, Scott, Murphy & Presser, PC

(57) ABSTRACT

A medical system includes: a treatment instrument having an insertion portion configured by an exterior member, and an insertion member that is inserted into the exterior member and is longer than the exterior member; an insertion portion inserting/pulling-out device to transmit a driving force to the exterior member or the insertion member configuring the insertion portion of the treatment instrument, the insertion portion inserting/pulling-out device advancing/retreating at least one of the exterior member and the insertion member; and a driving force non-transmitting portion provided to the insertion member, the driving force non-transmitting portion preventing a driving force of the insertion portion inserting/pulling-out device from being transmitted to the exterior member when the insertion member is moved by a predetermined distance.

23 Claims, 26 Drawing Sheets

(56) References Cited

FOREIGN PATENT DOCUMENTS

| JP | 09-108180 A | | 4/1997 | |
| JP | 09108180 A | * | 4/1997 | ............... A61B 1/00 |
| JP | 2003-265406 A | | 9/2003 | |
| JP | 2004-113541 | | 4/2004 | |
| JP | 2005-218497 | | 8/2005 | |
| JP | 2006-087474 | | 4/2006 | |

* cited by examiner

MEDICAL SYSTEM AND ENDOSCOPE SYSTEM

BACKGROUND OF THE INVENTION

1. Field of the Invention

The present invention relates to a medical system including a treatment instrument and an inserting/pulling-out device, and capable of performing advancing/retreating operations of an insertion portion included in the treatment instrument and functional operations of a function portion included in the treatment instrument, by rotating a pair of rollers included in the inserting/pulling-out device.

2. Description of Related Art

In recent years, endoscopes have been widely used in the medical field. With an endoscope in the medical field, an insertion portion is inserted into a body cavity of a subject in order to perform an observation. Also, with the endoscope, various treatments can be performed by leading a treatment instrument into the body cavity via a treatment instrument channel provided to the insertion portion.

When performing a treatment by inserting the treatment instrument into the treatment instrument channel of the endoscope, an operator leads the treatment instrument into the body cavity via the treatment instrument channel. In doing so, the operator manually inserts the treatment instrument into the treatment instrument channel, with one hand grasping an operation portion of the endoscope, while the other hand holding a sheath serving as an insertion portion of the treatment instrument. However, the work of manually inserting the elongate treatment instrument into the treatment instrument channel has been a troublesome work for the operator.

To improve such disadvantages, for example, Japanese Unexamined Patent Application Publication No. 2004-113541 discloses an insertion/pull-out apparatus for a long-sized treating element of an endoscope. This insertion/pull-out apparatus is a so-called automatic insertion device for treatment instrument, including a pair of feeding rollers to give a feed to the long-sized treating element, and a drive system to positively/reversely rotate and drive at least one of the pair of feeding rollers. Further, as an automatic insertion device for treatment instrument, Japanese Unexamined Patent Application Publication No. 2005-218497 discloses an endoscope treatment system capable of inserting/pulling a treatment instrument into/out from an endoscope in a short period of time, by controlling each of an advancing/retreating drive of a first advance/retreat mechanism and a second advance/retreat mechanism. The endoscope treatment system can advance and retreat the treatment instrument in a channel by setting a control means to a first mode to drive the first and second advancing/retreating mechanisms, thereby advancing and retreating both of a sheath section and an operation tube section. On the other hand, when the control means is set to a second mode, only the second advancing/retreating mechanism is driven to advance/retreat the operating tube section relative to the sheath section, to supply an operational driving force to a treating portion via transmission means.

However, providing the two advancing/retreating mechanisms increases the size of an operation section and complicates the control thereof. Therefore, a device is desired wherein one advancing/retreating mechanism can control a plurality of advancing/retreating elements of the sheath section or the operating tube section and the like.

SUMMARY OF THE INVENTION

A medical system includes: a treatment instrument having an insertion portion configured by an exterior member, and an insertion member that is inserted into the exterior member and is longer than the exterior member; an insertion portion inserting/pulling-out device to transmit a driving force to the exterior member or the insertion member configuring the insertion portion of the treatment instrument, the insertion portion inserting/pulling-out device advancing/retreating at least one of the exterior member and the insertion member; and a driving force non-transmitting portion provided to the insertion member, the driving force non-transmitting portion preventing a driving force of the insertion portion inserting/pulling-out device from being transmitted to the exterior member when the insertion member is moved by a predetermined distance.

The above and other objects, features and advantages of the invention will become more clearly understood from the following description referring to the accompanying drawings.

DETAILED DESCRIPTION OF PREFERRED EMBODIMENTS

Figure 1:
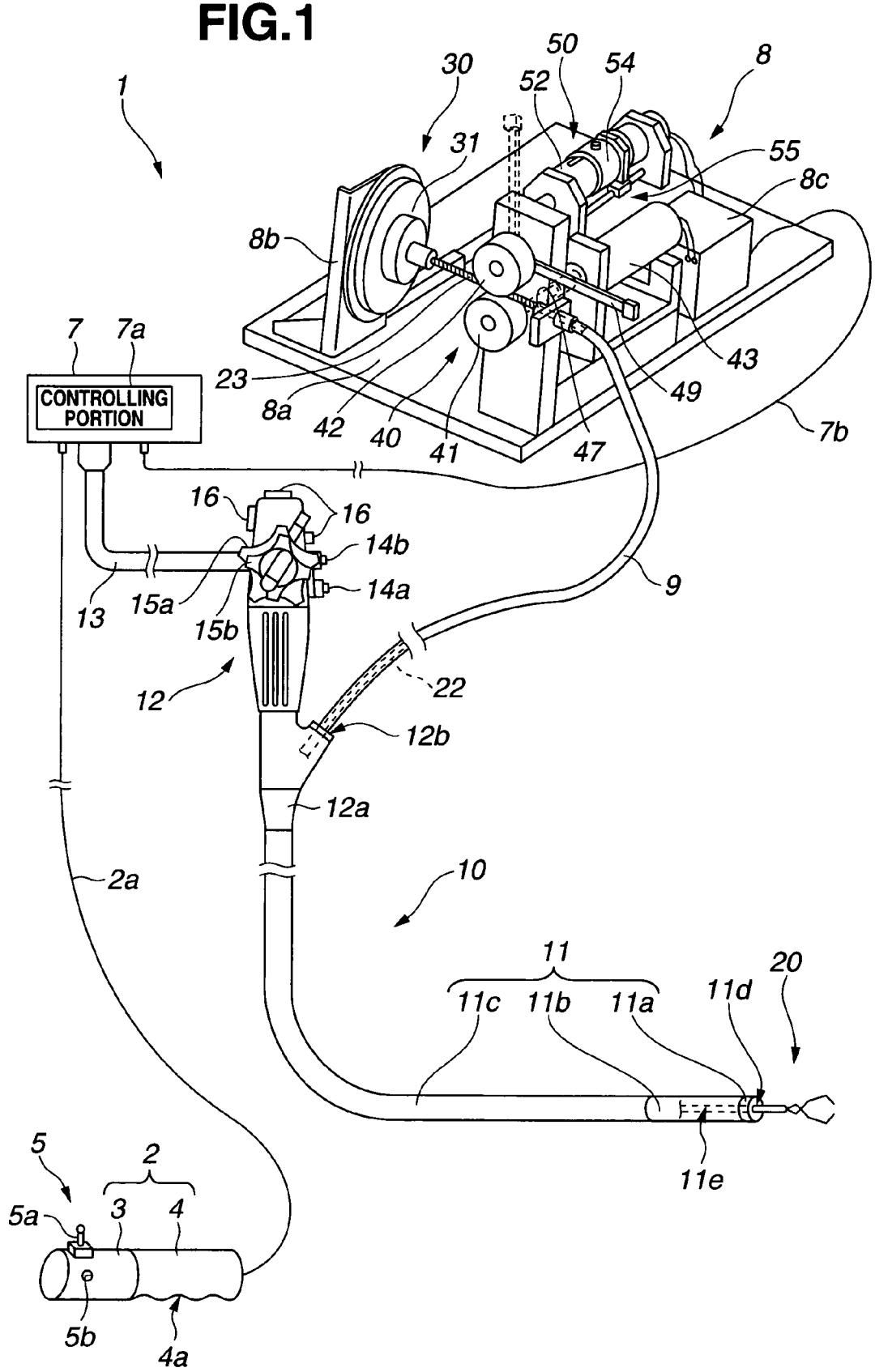
FIG. 1 is a view to illustrate an exemplary configuration of an endoscope system.

Referring to the drawings, an embodiment of the present invention will be described below.

Referring to FIGS. 1 to 19, a first embodiment of the present invention will be described.

First, referring to FIGS. 1 to 11, a configuration of an endoscope system I will be described.

As shown in FIG. 1, the endoscope system 1 serving as a medical device is configured mainly by: an operation instruction device 2; a control device 7 serving both as a light source device and a video processor; an electric operation device 8; an endoscope 10; and a treatment instrument 20 including an elongate sheath portion to be described later.

The operation instruction device 2 has a generally columnar shape, and is configured by a rigid main body portion 3 and a grip body 4 which is an elastic member, for example, to be continuously provided to the main body portion 3. The main body portion 3 and the grip body 4 are integrally configured by fitting a fitting protruding portion (not shown) provided to protrude from the center of a proximal end surface of the main body portion 3, into a fitting hole (not shown) provided at a distal end surface of the grip body 4. From a proximal end surface side of the grip body 4, a signal cable 2a is extended. The signal cable 2a has a proximal end side which is electrically connected to the control device 7.

On a side circumferential surface of the main body portion 3, an operation instructing portion 5 is provided. On the other hand, the grip body 4 is provided with a gripping portion 4a configured in a concave/convex shape. This allows an operator to surely grasp the operation instruction device 2 when grasping the gripping portion 4a. The gripping portion 4a is provided on the side circumferential surface in a positional relation opposite to the operation instructing portion 5 of the main body portion 3.

In the following description of the operation instruction device 2 thus configured, the distal end surface side of the main body portion 3 configuring the operation instruction device 2 will be described as a distal end side, and the proximal end surface side of the grip body 4 as a proximal end side.

The operation instructing portion 5 includes an operation lever 5a of a joystick type, for example, and a pressing switch 5b. When the operator operates to incline the operation lever 5a toward the distal end side, an instruction signal for advancing sheaths 22, 23 to be described later included in the treatment instrument 20 is outputted from the operation instructing portion 5 to a controlling portion 7a of the control device 7. When the operator operates to incline the operation lever 5a toward the proximal end side, an instruction signal for retreating the sheaths 22, 23 is outputted from the operation instructing portion 5 to the controlling portion 7a of the control device 7. On the other hand, when the pressing switch 5b is operated, an instruction signal for retreating an operation wire 24 to be described later is outputted from the operation instructing portion 5 to the controlling portion 7a of the control device 7.

The endoscope 10 is configured to include an insertion portion 11, an operation portion 12, and a universal cord 13. The operation portion 12 serves also as a gripping portion, and is provided on a proximal end side of the insertion portion 11. The universal cord 13 is extended from a side portion of the operation portion 12, and has a proximal end connected to the control device 7.

The insertion portion 11 is configured by, in the following order from the distal end side thereof, a rigid distal end portion 11a, a bendable bending portion 11b, and a flexible tube portion 11c having flexibility, which are continuously provided. The distal end portion 11a is provided with a treatment instrument lead-out hole 11d which is a distal end aperture, and an observation optical system, an illumination optical system and the like, not shown. The operation portion 12 is provided with a folding preventing portion 12a connected with a proximal end of the flexible tube portion 11c. On a distal end side of the operation portion 12, a treatment instrument lead-in port 12b is provided. On the proximal end side of the operation portion 12 are provided: an air/water button 14a for feeding air and water; a suction button 14b for performing suction; bending knobs 15a, 15b to be operated to bend the bending portion 11b; various switches 16 to control an endoscope image obtained by an image pickup device provided to the distal end portion 11a; and the like.

Note that the insertion portion 11 of the endoscope 10 includes a treatment instrument channel 11e communicating the treatment instrument lead-in port 12b and the treatment instrument lead-out hole 11d.

The control device 7 is provided with the controlling portion 7a, a lamp (not shown) for supplying illumination light, a signal processing circuit (not shown), and the like. The signal processing circuit performs processings such as generating a drive signal to drive an image pickup device (not shown) such as a CCD provided to the distal end portion 11a of the endoscope 10, and generating a video signal from an electric signal transmitted from the image pickup device. The control device 7 is connected with a display device such as a liquid crystal display (not shown) for displaying an endoscope image.

Figure 6:
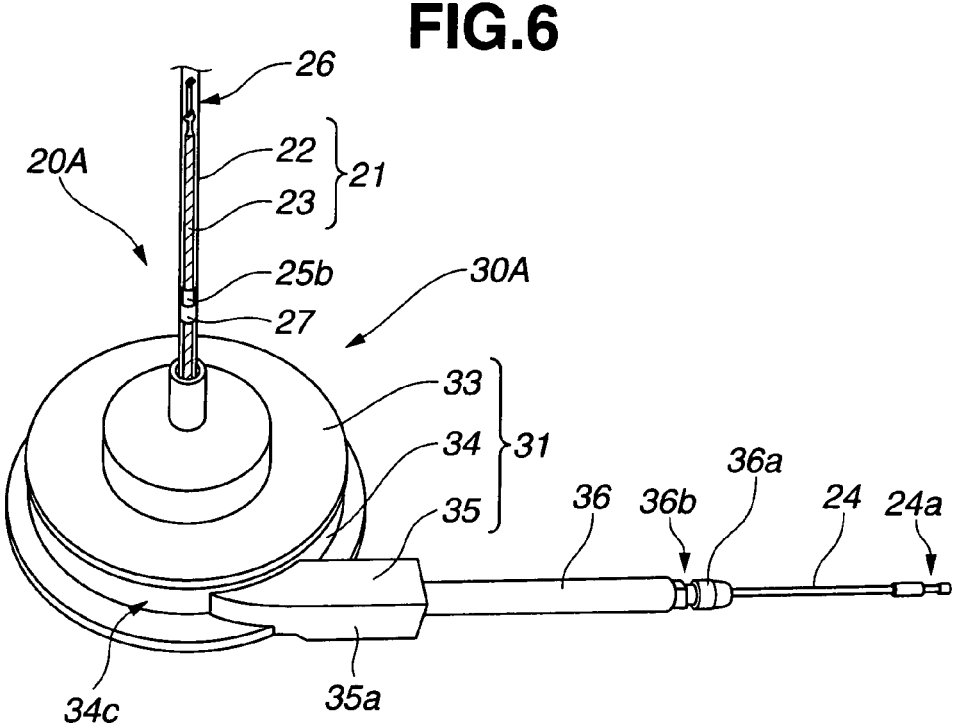
FIG. 6 is a view to illustrate a clip device cartridge including a clip device.
Figure 7:
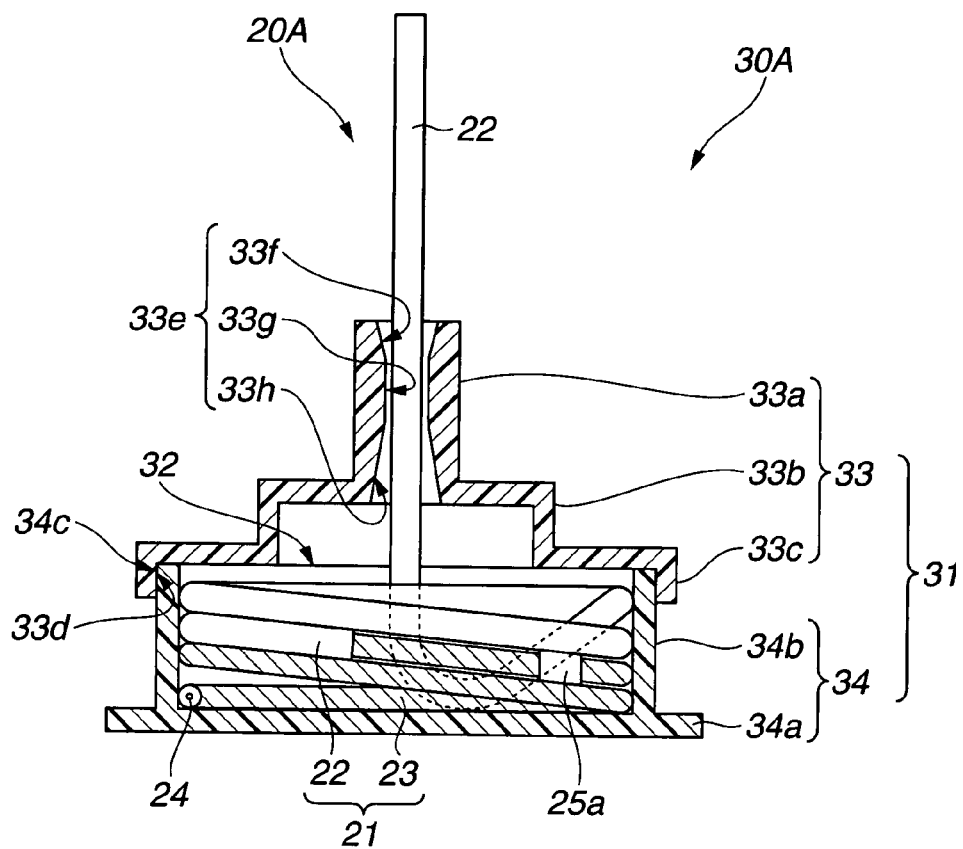
FIG. 7 is a cross sectional view to illustrate a configuration of a case main body, and a view to illustrate a housing state of a sheath portion housed in a sheath housing portion.

The treatment instrument 20 is configured as a treatment instrument cartridge 30 shown in FIGS. 6, 7. In a sheath housing portion 32 which is a housing space of a case main body 31 is housed a flexible sheath portion 21 configuring an insertion portion of the treatment instrument 20. The sheath portion 21 of the present embodiment is configured to include an outer sheath 22 which is an exterior member and a first sheath, and an inner sheath 23 which is an insertion member and a second sheath. From a sheath lead-out portion (hereinafter described as lead-out portion) 33a to be described later configuring the case main body 31, the outer sheath 22 configuring the treatment instrument 20 is extended. From a sheath proximal-end extension portion (hereinafter described as extension portion) 36 to be described later, an operation wire 24 is extended.

Note that the extension portion 36 has a proximal end portion provided with an extension portion connector 36a including a connection groove 36b. The operation wire 24 has a proximal end portion provided with an operation wire connector (hereinafter described as wire connector) 24a.

The case main body 31 can be detachably mounted to a treatment instrument mounting portion 8b provided on a table 8a of the electric operation device 8 shown in FIG. 1. To this end, for example, the treatment instrument mounting portion 8b is provided with a key, for example, to be located in a key groove not shown of the case main body 31. Reference symbol 8c designates an electric operation device controlling portion to be electrically connected to the control device 7.

Figure 2:
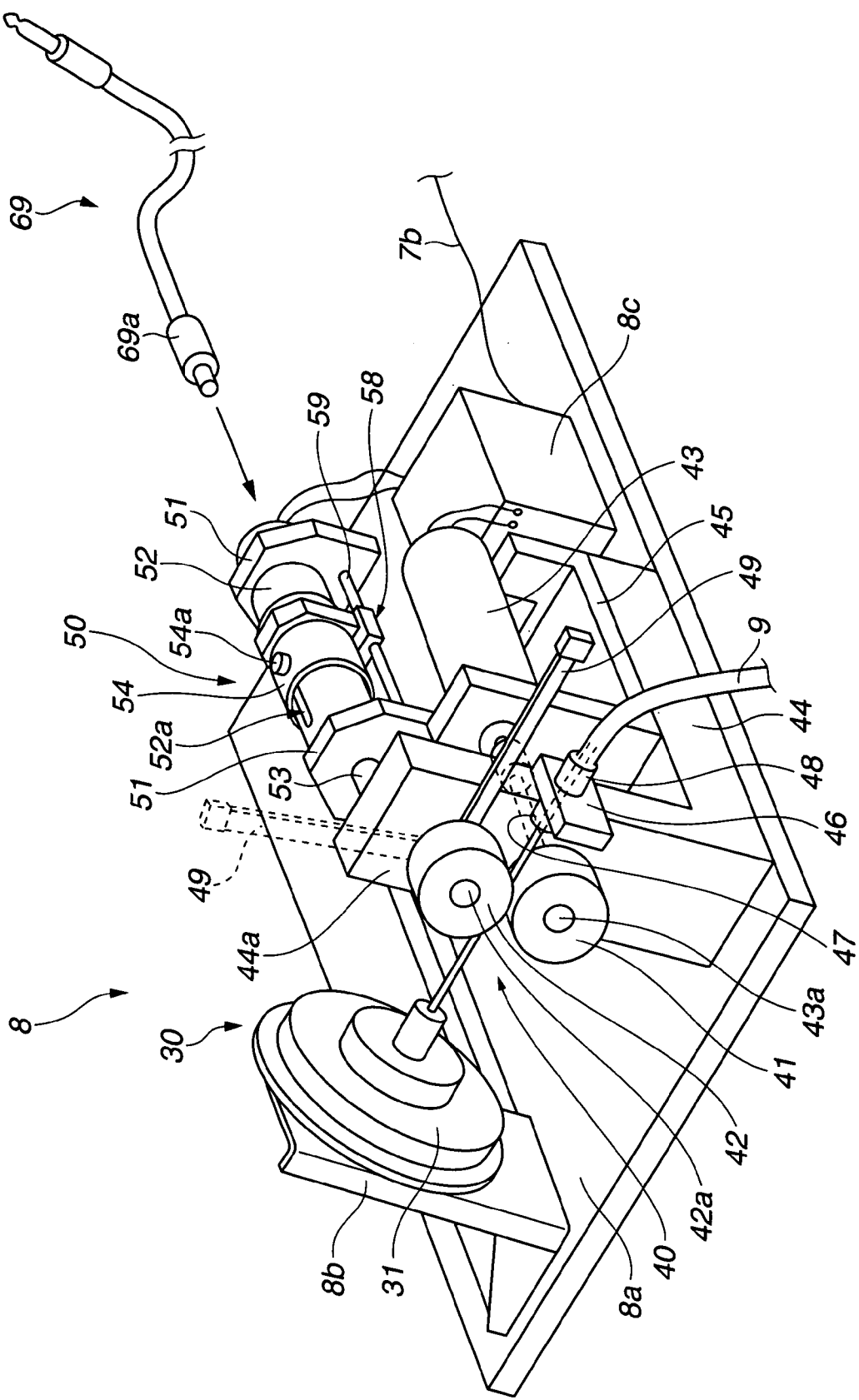
FIG. 2 is a view to illustrate an exemplary configuration of an electric operation device.

As shown in FIGS. 1, 2, the electric operation device 8 is configured to include, on the table 8a, the treatment instrument cartridge 30, an insertion portion inserting/pulling-out device (hereinafter described as inserting/pulling-out device) 40, and a function portion activating device (hereinafter described as activating device) 50.

The inserting/pulling-out device 40 is mainly configured to include a pair of rotatable rollers 41, 42, a roller motor (hereinafter described as first motor) 43. The inserting/pulling-out device 40 is installed on the table 8a via an inserting/pulling-out device fixture table 44.

The rollers 41, 42 are provided to a roller disposing portion 44a of the inserting/pulling-out device fixture table 44. The first motor 43 is mounted to a motor fixture table 45 fixed to the inserting/pulling-out device fixture table 44. Near the rollers 41, 42 of the roller disposing portion 44a, an attachment board 46 having a penetrating hole is fixed. A roller-side aperture of the penetrating hole provided to the attachment board 46 is provided with a spigot body 47 serving as an exterior member holding portion. The other side of the aperture is provided with a tube attaching portion 48 to which a connection tube 9 is mounted. The connection tube 9 is a flexible tube formed of tetrafluoro-ethylene resin or the like. The spigot body 47 is configured by a rubber member having a predetermined elasticity, and closely contacts an outer circumferential surface of the outer sheath 22 inserted through the spigot body 47 so as to apply a predetermined resistance force to the outer-sheath 22.

The rollers 41, 42 are each configured by an elastic resin member to be adaptable to the sheaths 22, 23 having different diameter dimensions configuring the sheath portion 21. The roller 41 is mounted to a motor shaft 43a, and the roller 42 is integrally fixed to a driven shaft 42a rotatably provided to the roller disposing portion 44a.

Reference symbol 49 designates a roller opening/closing lever (hereinafter described as opening/closing lever). By locating the opening/closing lever 49 at a nipping state position shown in a solid line, the rollers 41, 42 are turned to a closed state, so as to press and nip outer surfaces of the sheaths 22, 23. On the other hand, by locating the opening/closing lever 49 at a released position shown in a broken line, the rollers 41, 42 are turned to an open state, that is, the interval between the rollers 41, 42 is expanded to facilitate locating the outer sheath 22. When the opening/closing lever 49 is turned to a closed state to turn the rollers 41, 42 to the nipping state, the interval between the rollers 41, 42 is smaller than an outer diameter dimension of the inner sheath having a small diameter dimension.

According to this configuration, in a state where the distance between the rollers 41, 42 is expanded, a distal end of the outer sheath 22 configuring the sheath portion 21 extended from the case main body 31 is located in the connection tube 9 via the spigot body 47, the attachment board 46, and the tube attaching portion 48. Then, the outer sheath 22 is pressed and nipped by the rollers 41, 42. In this nipping state, the first motor 43 is driven and rotated in a predetermined direction to rotate the roller 41, to advance/retreat and thus move back/forth the sheaths 22, 23 along with the rotation of the roller 41 in the treatment instrument channel 11e, for example, as described below. In other words, by a drive control of the first motor 43, the sheaths 22, 23 of the treatment instrument 20 are advanced in the treatment instrument channel 11e toward inside of a body cavity, and retreated to be pulled out of the body cavity. Note that the drive control of the first motor 43 is performed by the controlling portion 7a of the control device 7 based on an operation of the operation lever 5a.

Referring to FIGS. 1 to 5, the activating device 50 will be described.

As shown in FIGS. 1, 2, the activating device 50 is installed on the table 8a via a pair of mounting tables 51. The activating device 50 is configured to include a slide seat 52 which is a tubular device body, an extension portion fixing portion 53, a slider portion 54, and a driving portion 55. The slider portion 54 integrally includes an operation wire fixing portion 56. The slider portion 54 includes a fixing knob 54a for attachably/detachably connecting the operation wire 24.

The driving portion 55 is mainly configured to include a slider driving motor (hereinafter described as second motor) 57, a driving force transmitting portion (hereinafter described as transmitting portion) 58 including a gear box 58a, and a rack 59. The transmitting portion 58 has a fixing portion 58b integrally fixed to the slider portion 54. In the gear box 58a of the transmitting portion 58, there is equipped a line of gears not shown with which to slide the slider portion 54 in a longitudinal axial direction by means of driving force of the second motor 57.

Figure 3:
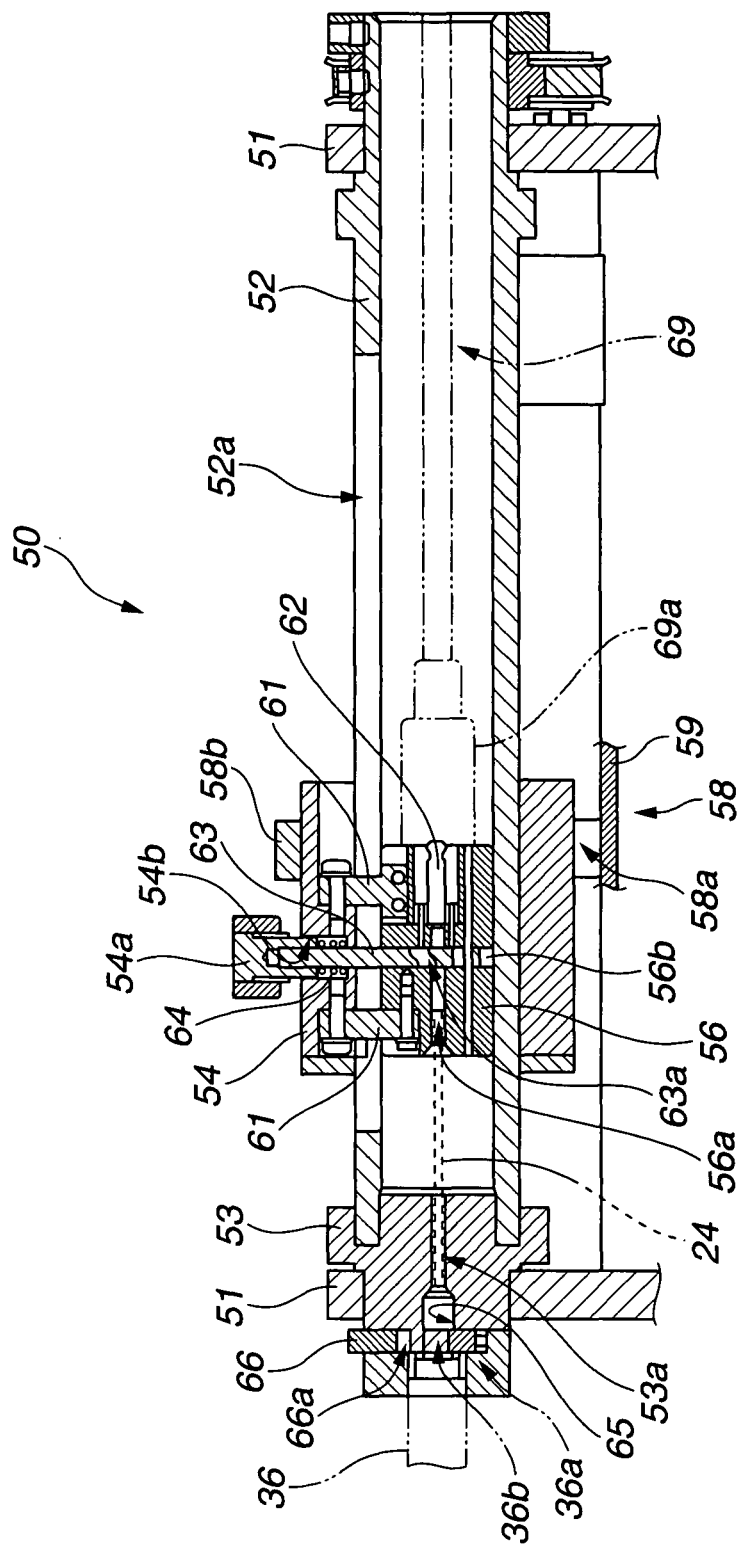
FIG. 3 is a cross sectional view of essential parts to illustrate an inner structure of an activating device.
Figure 4:
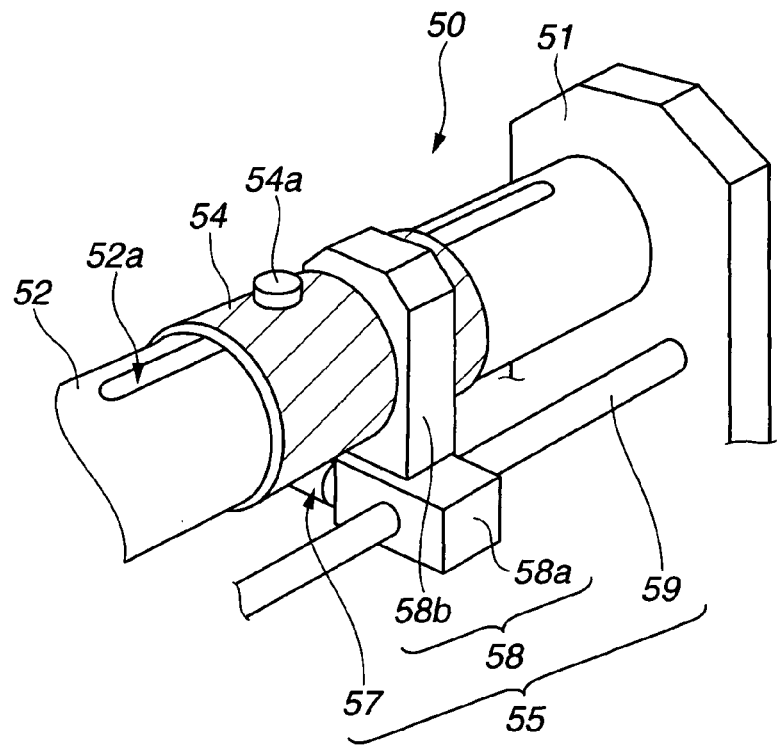
FIG. 4 is a perspective view to illustrate a configuration near a slider portion of the activating device.
Figure 5:
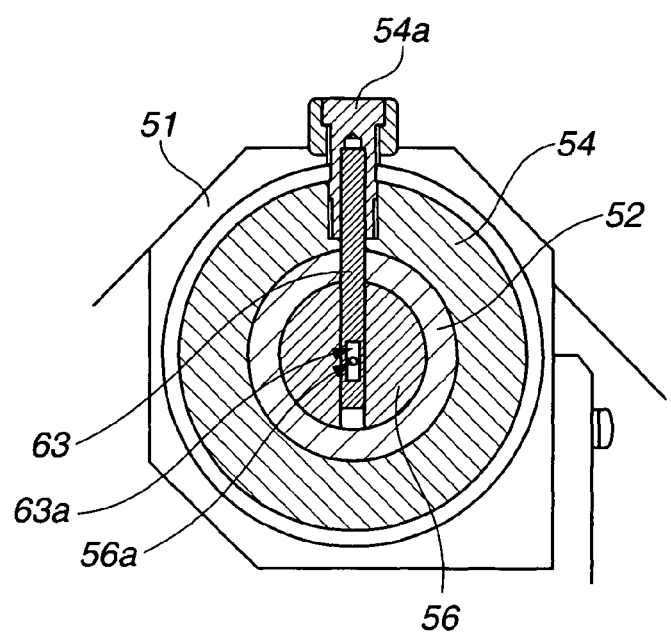
FIG. 5 is a cross sectional view to illustrate a configuration including a fixing knob at the slider portion of the activating device.

As shown in FIGS. 3, 4, 5, the slide seat 52 includes a long hole 52a formed in parallel with a longitudinal axial direction thereof. On one end side of the slide seat 52, the extension portion fixing portion 53 is fixed. On an outer circumference of the slide seat 52, the tubular slider portion 54 is slidably located. In an inner hole of the slide seat 52, the operation wire fixing portion 56 is disposed. The slider portion 54 and the operation wire fixing portion 56 are integrally fixed to each other through a pair of connection blocks 61 inserted and located through the long hole 52a.

On one end side of the operation wire fixing portion 56, that is the side toward the extension portion fixing portion 53, there is formed an operation wire inserting hole (hereinafter described as wire hole) 56a coaxially with a longitudinally directed center axis of the slide seat 52. On the other side of the operation wire fixing portion 56, on the other hand, there is provided a plug 62 coaxially with a longitudinally directed center axis of the slide seat 52. The plug 62 is connected with an active cord 69 (see FIG. 2), which is connected by one end to a high-frequency generating device, in attachable/detachable manner by an other end portion 69a. The plug 62 is configured to be rotatable relative to the operation wire fixing portion 56 provided with a slip ring or the like, thus preventing torsion or the like of the active cord 69.

To the slider portion 54 and the operation wire fixing portion 56 are respectively formed penetrating holes 54b, 56b having a center axis orthogonal to the longitudinal axial direction. In the penetrating holes 54b, 56b is slidably disposed an operation wire connection rod (hereinafter described as wire connection rod) 63 having one end fixed to the fixing knob 54a. To a distal end of the wire connection rod 63 is formed a connector hole 63a as a penetrating hole in which the wire connector 24a can be located.

Reference symbol 64 designates a push spring having an urging force to push the fixing knob 54a upward in the drawing. By pressing the fixing knob 54a downward in the drawing against the urging force of the push spring 64, the wire connection rod 63 is moved, resulting in a general match between the center axis of the connector hole 63a formed in the wire connection rod 63 and the center axis of the wire hole 56a, thereby communicating the holes to each other.

To the extension portion fixing portion 53 is formed a wire hole 53a through which the operation wire 24 is inserted. The wire hole 53a has a center axis agreeing with the longitudinally directed center axis of the slide seat 52. To one end of the wire hole 53a is provided an extension portion connecting portion 65 to be connected with the extension portion connector 36a included by the extension portion 36.

To the extension portion connecting portion 65 is located a connecting plate 66 including a hole 66a, which is slidable in a direction orthogonal to the center axis of the wire hole 53a. When the extension portion connector 36a is inserted into the extension portion connecting portion 65, to be located at a predetermined position, the connecting plate 66 is moved by an urging force of an application member not shown, to cause a peripheral portion of the hole 66a of the connecting plate 66 to be engaged, with a click feel, with and located in the connection groove 36b.

The case main body 31 includes a first member 33, a second member 34, and a sheath proximal-end fixing portion 35, as shown in FIG. 6. The first member 33 and the second member 34 are configured to be integrally connected by screwing, for example. At least one of the members 33, 34 configuring the case main body 31 is preferably configured with a transparent or semi-transparent resin member. This allows the operator to visually check a housing state or the like of the sheaths 22, 23 housed in the sheath housing portion 32 through the first member 33 or the second member 34.

Referring to FIG. 7, specific configuration of the case main body 31 will be described.

The second member 34 includes a plate portion 34a and an annular portion 34b, for example. Inside of the annular portion 34b is a space for housing the sheaths 22, 23. The annular portion 34b has an inner circumferential surface configured as a housing surface with which the sheaths 22, 23 located in the annular portion 34b come in contact. Accordingly, the annular portion 34b has an inner diameter dimension which is set in consideration of a length dimension and so-called repulsion force of the sheaths 22, 23 configuring the treatment instrument 20. To the annular portion 34b is formed a hole not shown for communicating inner and outer circumferential surfaces thereof. On an outer circumferential surface on the aperture side of the annular portion 34b, a male screw 34c is formed.

The plate portion 34a has, for example, a circular shape. A flat surface of the plate portion 34a inside the annular portion 34b is a guiding surface impinged mainly by the inner sheath 23. Note that the plate portion 34a is not limited to a circular shape, and may have a polygonal shape such as square or regular hexagonal shape, for example.

The sheath proximal-end fixing portion 35 shown in FIG. 6 has a generally rectangular parallelepiped shape. One side surface 35a of the sheath proximal-end fixing portion 35 is integrally fixed to the second member 34 by adhesion or welding and the like, in a positional relation to generally contact an outer circumferential surface 34c of the annular portion 34b. To the sheath proximal-end fixing portion 35 is provided, in a longitudinal direction thereof, with elongate first and second hole portions (not shown). To the first hole portion, a proximal end of the inner sheath 23 is fixed. To the second hole portion, a distal end of the extension portion 36 is fixed. The first and second hole portions have coaxial centers, and communicate to each other to configure a penetrating hole. When the sheath proximal-end fixing portion 35 is fixed to the second member 34, the penetrating hole of the sheath proximal-end fixing portion 35 is in communication with the hole of the annular portion 34b.

On the other hand, the first member 33 is a stepped cylindrical member, as shown in FIG. 7. The first member 33 includes, in the following order with increasingly larger outer diameter from one end side, the lead-out portion 33a, a lead-out portion guiding-space forming portion (hereinafter described as guiding portion) 33b, and a lid portion 33c. The lid portion 33c, the guiding portion 33b, and the lead-out portion 33a are coaxially formed. The guiding portion 33b is provided to prevent formation of a winding part to the sheaths 22, 23, when the sheaths 22, 23 rolled in the sheath housing portion 32 are being forwarded therefrom to the lead-out hole 33e.

The lid portion 33c has an inner circumferential surface on which is formed a female screw 33d to be screwed with the male screw 34c of the annular portion 34b. At the center of the lead-out portion 33a, a lead-out hole 33e is formed.

By screwing the female screw 33d of the lid portion 33c with the male screw 34c of the annular portion 34b, the first member 33 is fixed to the second member 34 integrated with the sheath proximal-end fixing portion 35, to configure the case main body 31 having the sheath housing portion 32.

The sheath housing portion 32 of the case main body 31 has an inner diameter dimension that is set in consideration of repulsion force of the sheaths 22, 23. Accordingly, the sheaths 22, 23 rolled and located in the sheath housing portion 32 will, with the repulsion force of the sheaths 22, 23, expand outwardly in a direction to cancel the rolled state. Thus, the sheaths 22, 23 are located in the sheath housing portion 32, pressed against the inner circumferential surface of the annular portion 34b.

Note that the annular portion 34b has a height dimension that is set in consideration of diameter and length dimensions of the sheaths 22, 23. This allows the sheaths 22, 23 rolled and housed in the sheath housing portion 32 to be stably housed therein, in close contact with the inner circumferential surface of the annular portion 34b.

Reference symbol 33e designates a sheath lead-out hole 33e including, in the following order from a distal end side, a lead-in guiding surface 33f, a communication hole 33g, and a lead-out guiding surface 33h. The lead-in guiding surface 33f and the lead-out guiding surface 33h are guiding surfaces to allows for smooth passage of a contact member (hereinafter described as contact ring) 25a to be described later through the sheath lead-out hole 33e, and are formed in taper shape with larger diameter dimension from the communication hole 33g toward respective end surface apertures. The communication hole 33g has a diameter larger than an outer diameter of the contact ring 25a.

In the present embodiment, the treatment instrument 20 is a clip device 20A and the treatment instrument cartridge 30 is a clip device cartridge 30A.

Referring to FIGS. 6 to 9, the clip device 20A equipped to the clip device cartridge 30A is described.

Figure 8:
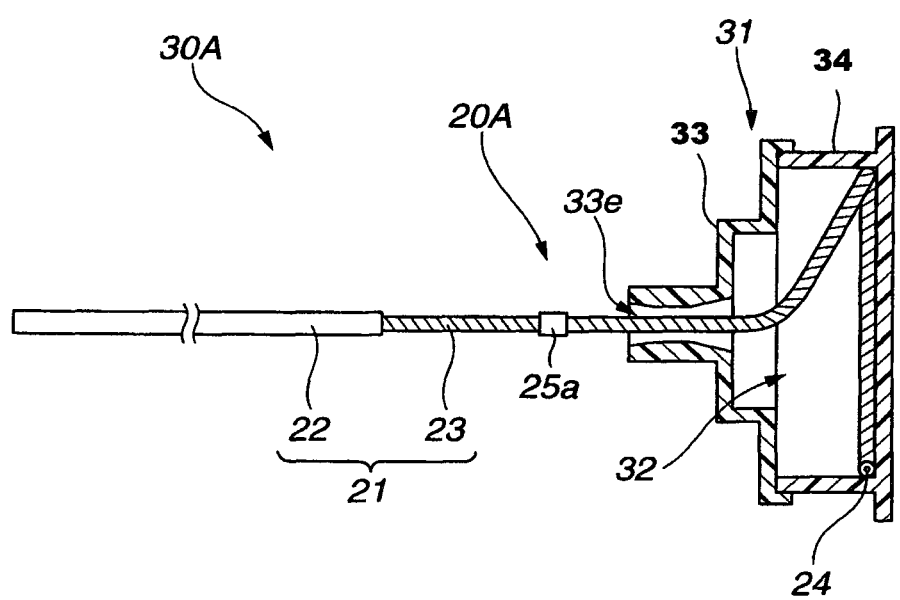
FIG. 8 is a view to illustrate a state where the sheath portion is being led out from a lead-out hole of the case main body.

As shown in FIGS. 6 to 8, the clip device 20A includes the sheath portion 21 housed in the sheath housing portion 32 of the case main body 31. The sheath portion 21 is configured to include the outer sheath 22 which is an elastic tube body having a hollow portion in a longitudinal axial direction, and the inner sheath 23 configured by a coil sheath which is advanceably and retreatably inserted in the hollow portion of the outer sheath 22 and which has flexibility and a hollow portion in a longitudinal axial direction. In the inner sheath 23, the operation wire 24 is slidably located. The proximal end side of the inner sheath 23 extends from a proximal end side of the outer sheath 22. The operation wire 24 has a proximal end side extending from the inner sheath 23 and extended to outside of the case main body 31, passing in through the penetrating hole of the sheath proximal-end fixing portion 35 and the extension portion 36.

At a halfway portion of the inner sheath 23 exposed from a proximal end side of the outer sheath 22, the contact ring 25a with a ring shape is fixed. The contact ring 25a is a contact member configuring a rotational driving force non-transmitting portion. The contact ring 25a is fixed to the inner sheath 23 so as to contact the proximal end surface of the outer sheath 22 when the inner sheath 23 is advanced with respect to the outer sheath 22 to reach a predetermined moving distance. The contact ring 25a serves also as a moving distance setting member.

Figure 9:
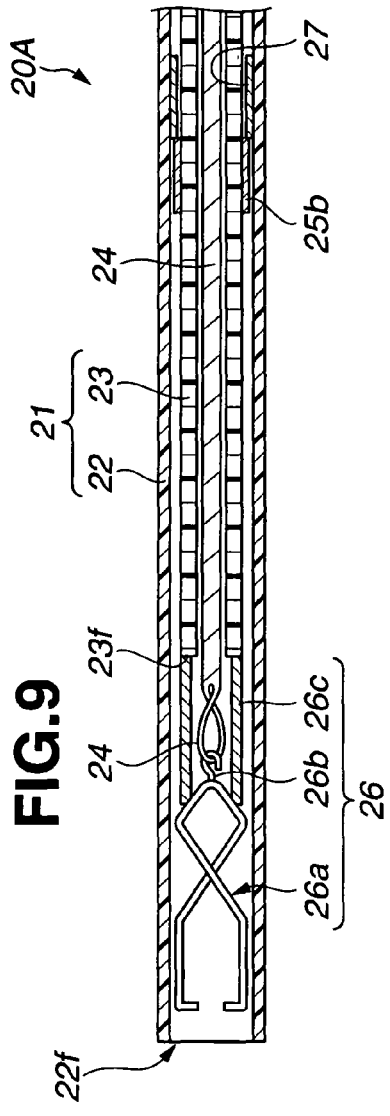
FIG. 9 is a cross sectional view to illustrate a configuration of a distal end portion of the clip device.

Specifically, the moving distance of the contact ring 25a is set so that, in a state where a clip unit 26 is positioned at a distal end 23f of the inner sheath 23 and is housed in a distal end portion of the outer sheath 22 as shown in FIG. 9, a distal end surface of the inner sheath 23 protrudes from the distal end surface 22f of the outer sheath 22 when the inner sheath 23 is advanced.

As shown in FIG. 9, in the distal end portion of the outer sheath 22, the clip unit 26 is located. The clip unit 26 is a functional portion, including a clip 26a, a hook portion 26b, and a clip-tightening tube portion (hereinafter described as tightening tube) 26c. The hook portion 26b is located in the outer sheath 22, in a state of being hooked on a loop 24b provided at a distal end of the operation wire 24.

On an outer surface at a predetermined position on a distal end side of the inner sheath 23, a ring-shaped engaging member (hereinafter described as engaging ring) 25b is fixed. On the other hand, on an inner surface at a predetermined position on a distal end side of the outer sheath 22, a ring-shaped stopper member 27 is provided. The stopper member 27 is an advancing/retreating movement switching function portion, is a movement restricting member for restricting the engaging ring 25b from moving closer to the proximal end side than the stopper member 27, and is configured so that a proximal end surface of the ring-shaped engaging member 25b comes in contact with a distal end surface of the stopper member 27. The contact member 25a, the engaging ring 25b, and the stopper member 27 provide a first sheath motion mechanism portion.

In a state where the engaging ring 25b is in contact with the stopper member 27, the clip unit 26 is positioned at the distal end of the inner sheath 23, and is located in the distal end portion of the outer sheath 22 near the distal end surface 22f, as shown in FIG. 9. That is, the engaging ring 25b is an advancing/retreating movement switching mechanism portion, and is a positioning member for setting a position of the distal end portion of the inner sheath 23 in the distal end portion of the outer sheath 22.

Figure 10:
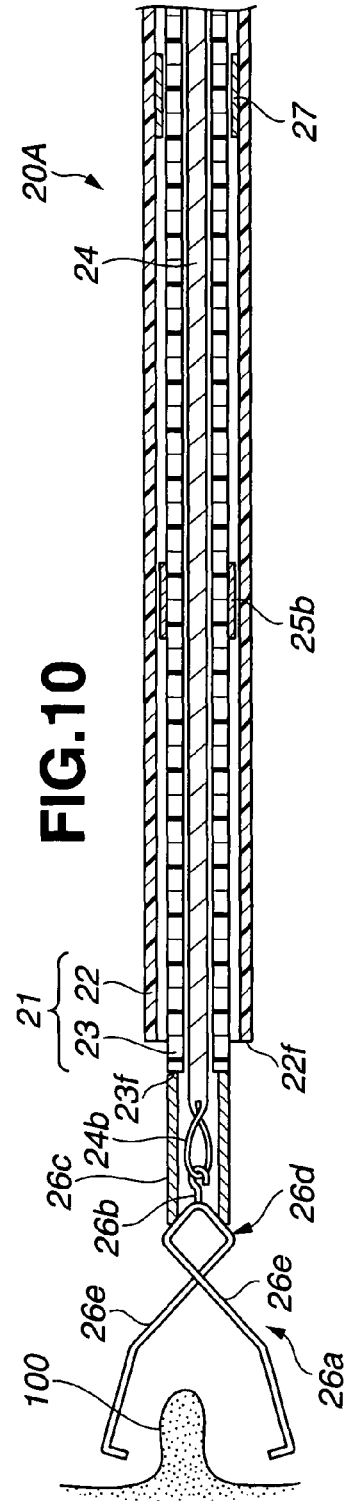
FIG. 10 is a cross sectional view to illustrate the distal end portion of the clip device in a state where a clip unit is protruded from an outer sheath.
Figure 11:
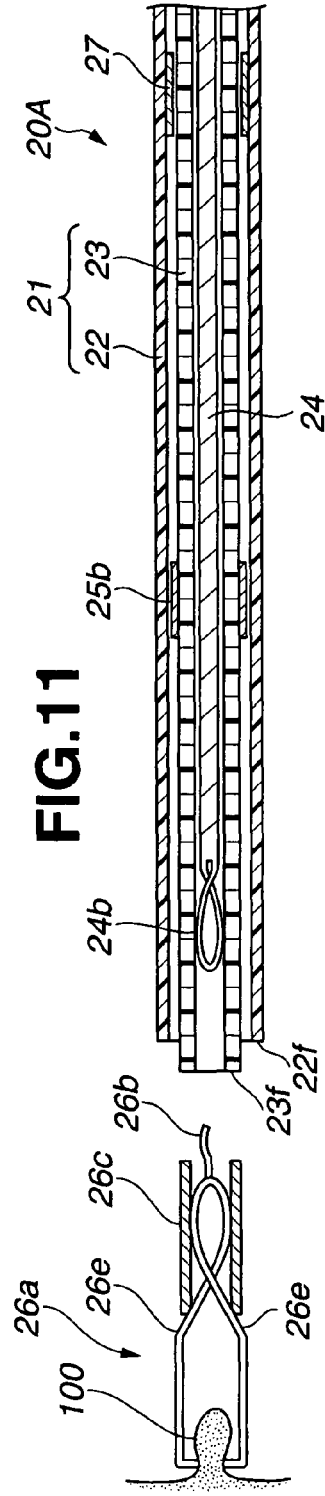
FIG. 11 is a cross sectional view to illustrate the distal end portion of the clip device in a state where a clip of the clip unit is placed at a target region.

Referring to FIGS. 10, 11, there will be described actions to place the clip of the clip unit to a target region.

Note that the clip unit 26 located in the distal end portion of the outer sheath 22 as shown in FIG. 9 is protruded from the distal end surface 22f of the outer sheath 22 by advancing the inner sheath 23 with respect to the outer sheath 22.

When it is completed to locate the clip 26a to a target region 100, the operation wire 24 is towed by a predetermined amount toward the hand side, while retaining the protrusion state of the inner sheath 23.

By the towing of the operation wire 24, an opening motion portion 26d having a rhombus shape is pulled into the tightening tube 26c, being pushed and pressed therein. As the opening motion portion 26d is pressed, the clip 26a gradually changes into an expanded state into a fully opened state.

Then, by further towing the operation wire 24, an inclined wall 26e included in the clip 26a is pulled into the tightening tube 26c, deforming the clip 26a to a closed state.

By further continuing the towing of the operation wire 24, the hook portion 26b with a J-shape is subject to plastic deformation into an I-shape, detaching the hook portion 26b from the loop 24b as shown in FIG. 11, which results in the clip 26a deformed into a closed state to be placed at the target region 100. After this, the tow amount of the operation wire 24 reaches a predetermined amount.

Here, there will be described procedures of housing the sheath portion 21 of the clip device 20A into the sheath housing portion 32 of the case main body 31, to configure the clip device cartridge 30A.

First, a worker prepares: the outer sheath 22 provided with the stopper member 27, the inner sheath 23 provided with the engaging ring 25b, the operation wire 24, the contact ring 25a, and the clip unit 26 which configure the clip device 20A sterilized; the first member 33 and the second member 34 integral with the sheath proximal-end fixing portion 35, which configure the case main body 31; and so forth. Note that the length dimension of the outer sheath 22 is set in consideration of length dimension of the treatment instrument channel 11e equipped to the endoscope 10, length dimension of the connection tube 9, thickness of the attachment board 46, length dimension of the spigot body 47, and the like. The stopper member 27 is integrally provided at a predetermined position on an inner circumferential surface of the distal end portion of the outer sheath 22. On the other hand, the length dimension of the inner sheath 23 is set to be longer than the length dimension of the outer sheath 22 by a predetermined dimension. The engaging ring 25b is integrally provided at predetermined position on an outer circumferential surface of a distal end portion of the inner sheath 23.

Next, the worker inserts the proximal end side of the inner sheath 23 into an aperture on the distal end side of the outer sheath 22, and feeds the inner sheath 23 toward a proximal end of the outer sheath 22. Then, a proximal end portion of the inner sheath 23 is externally led out from an aperture at the proximal end of the outer sheath 22. Subsequently, by grasping a proximal end portion of the outer sheath 22 to pull out the inner sheath 23 from the outer sheath 22, the proximal end surface of the engaging ring 25b is caused to contact the distal end surface of the stopper member 27, thus locating the inner sheath 23 at the distal end portion of the outer sheath 22 in a predetermined state.

Next, the worker inserts the operation wire 24 having the loop 24b through an aperture at the proximal end of the inner sheath 23 extended from the outer sheath 22, to feed the operation wire 24 toward the distal end of the inner sheath 23.

This causes the loop 24b to be led out from the distal end aperture of the inner sheath 23 to inside of the distal end portion of the outer sheath 22, and then externally led out from the distal end aperture of the outer sheath 22. Here, the worker hooks the hook portion 26b of the clip unit 26 on the externally exposed loop 24b, and tows the operation wire 24 to the hand side to locate the clip unit 26 at the distal end portion of the outer sheath 22 as shown in FIG. 9. Then, the worker fixes the contact ring 25a on an outer circumferential surface on the proximal end side of the inner sheath 23, in consideration of the protrusion amount of the clip unit 26.

Next, the worker prepares the second member 34, and then inserts the proximal end side of the operation wire 24 to the penetrating hole of the sheath proximal-end fixing portion 35 as shown in FIG. 6, to lead the proximal end side of the operation wire 24 out of the extension portion 36, and subsequently fixes, by adhesion for example, the proximal end portion of the inner sheath 23 to the first hole portion formed to the sheath proximal-end fixing portion 35.

Next, the worker houses the sheaths 22, 23 in a rolled state in the annular portion 34b of the second member 34, in the following order: the inner sheath 23 exposed from the outer sheath 22 and the outer sheath 22 in which the inner sheath 23 is inserted. As a result, the inner sheath 23 and the outer sheath 22, with repulsion force of the sheaths 22, 23, is housed in a rolled state in contact with the housing surface of the annular portion 34b.

Next, the worker inserts a distal end side portion of the outer sheath 22 in which the inner sheath 23 is inserted, to the lead-out hole 33e from the side of the lead-out guiding surface 33h, to expose the distal end portion of the outer sheath 22 by a predetermined amount from a distal end surface of the sheath lead-out hole 33e. The worker then screws the female screw 33d of the first member 33 to the male screw 34c of the second member 34, to integrally fix the first member 33 and the second member 34.

Thus is configured the clip device cartridge 30A wherein the clip unit 26 is included inside of the distal end portion of the outer sheath 22 as shown in FIG. 6, and the outer sheath 22 and the inner sheath 23 are housed in the sheath housing portion 32 of the case main body 31 as shown in FIG. 7.

Referring to FIGS. 12 to 19, there will be described actions of the endoscope system 1 wherein the clip device cartridge 30A configured as mentioned above is attached to the treatment instrument mounting portion 8b.

First, in performing an operation, a medical staff prepares one or a plurality of the clip device cartridges 30A each serving as a treatment instrument cartridge housing a treatment instrument for use in the operation. Then, the staff tentatively locates the case main body 31 configuring the clip device cartridge 30A to the treatment instrument mounting portion 8b equipped to the electric operation device 8.

Here, the staff connects the operation wire connector 24a to the operation wire fixing portion 56 as mentioned above, and then locates the case main body 31 at a predetermined position of the treatment instrument mounting portion 8b, to connect the extension portion connector 36a to the extension portion fixing portion 53. The staff also mounts the spigot body 47 compatible with the outer sheath 22 to the attachment board 46 equipped to the inserting/pulling-out device 40, and also mounts the connection tube 9, of which one end portion is connected to the treatment instrument lead-in port 12b, to the tube attaching portion 48 by the other end portion. The staff further electrically connects the signal cable 2a of the operation instruction device 2 to the control device 7, and electrically connects the control device 7 and the electric operation device 8 with a signal cable 7b.

Figure 12:
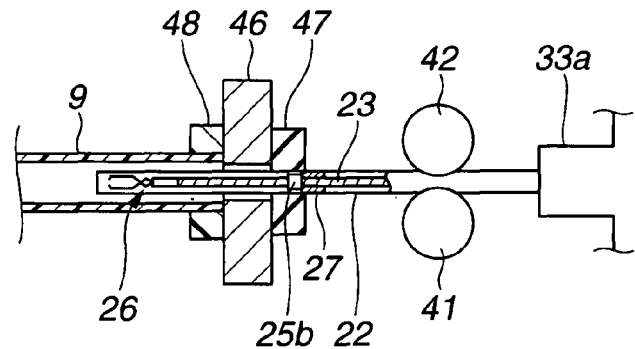
FIG. 12 is a view to illustrate a state where the outer sheath of the clip device is nipped by rollers.

Next, the staff proceeds to the work of locating between the rollers 41, 42 the outer sheath 22 exposed from the distal end surface of the sheath lead-out portion 33a. That is, the staff moves the opening/closing lever 49 to the position shown in the broken line to expand the interval between the rollers 41, 42, and introduces the distal end of the outer sheath 22 extended from the case main body 31 via between the rollers 41, 42 and through the spigot body 47, the attachment board 46, and the tube attaching portion 48, to located the distal end in the connection tube 9. The staff then operates to return the opening/closing lever 49 to the position shown in the solid line, so that the outer sheath 22 is nipped between the rollers 41, 42 as shown in FIG. 12. This completes the pre-operation preparation.

When using the clip device 20A after specifying a target region by performing endoscopic observation, the operator operates to incline the operation lever 5a of the operation instruction device 2 toward the distal end side, to lead the sheath portion 21 into the body cavity.

Figure 13:
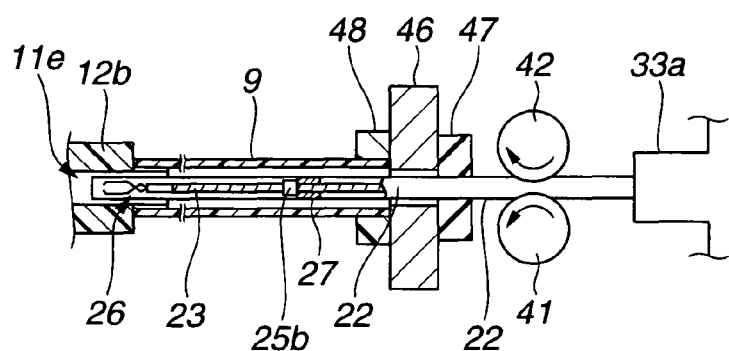
FIG. 13 is a view to illustrate a state where the outer sheath of the clip device is being advanced by the rollers.

The operator operates the operation lever 5a to rotate and drive the first motor 43 in a predetermined direction, causing the roller 41 to rotate as shown in an arrow in FIG. 13. As the roller 41 is rotated, the outer sheath 22 is advanced along with the rotation of the roller 41 against an urging force of the spigot body 47. The advancement of the outer sheath 22 causes the distal end surface of the stopper member 27 to contact the proximal end surface of the engaging ring 25b, thereby transmitting an advancing force to the inner sheath 23, and integrally advancing the inner sheath 23 and the outer sheath 22.

Then, the outer sheath 22 and the inner sheath 23 pass through the treatment instrument lead-in port 12b provided to the operation portion 12 of the endoscope 10, to be inserted and subsequently advanced in the treatment instrument channel 11e.

Figure 14:
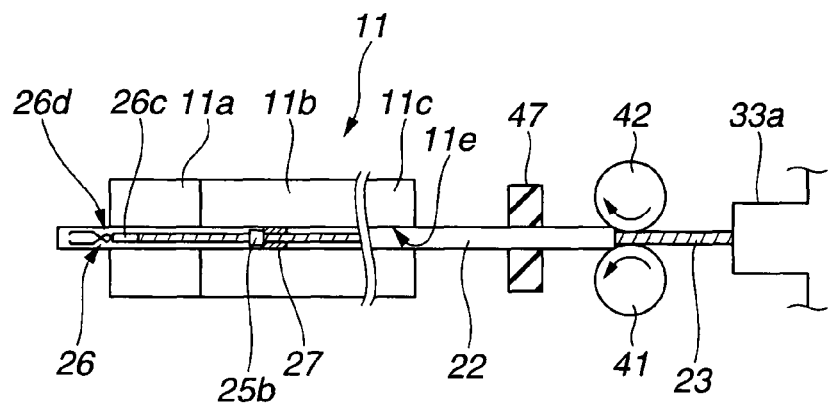
FIG. 14 is a view to illustrate a state where an inner sheath, instead of the outer sheath, is nipped by the rollers.

The distal end portion of the outer sheath 22 advancing in the treatment instrument channel 11e is led out into the body cavity from the distal end surface of the distal end portion 11a as shown in FIG. 14. Simultaneously with the distal end portion of the outer sheath 22 being led out, the inner sheath 23, instead of the outer sheath 22, is nipped between the rollers 41, 42.

Figure 15:
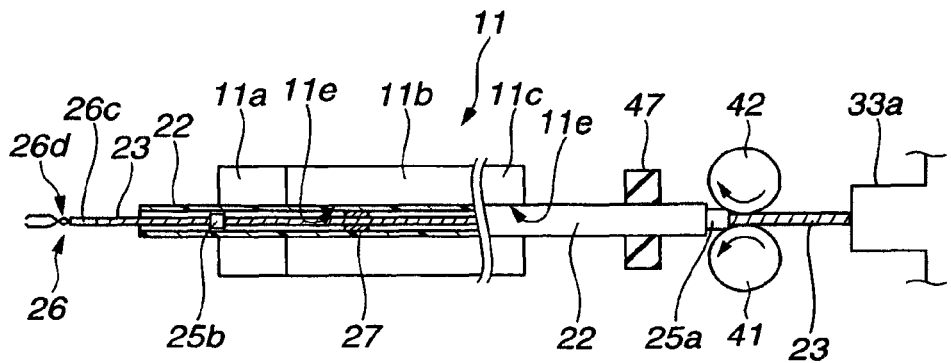
FIG. 15 is a view to illustrate a state where the inner sheath is advanced by the rollers, and the clip unit is protruded from the outer sheath.

This causes the inner sheath 23 to advance in the outer sheath 22 as the roller 41 rotates, protruding the clip unit 26 from the outer sheath 22, followed by the inner sheath 23 also being led out into the body cavity. Then, as shown in FIG. 15, the contact ring 25a passes through between the rollers 41, 42, and with the distal end surface of the contact ring 25a coming into contact with the proximal end surface of the outer sheath 22, the outer sheath 22 is advanced by the length of the contact ring 25a. This results in a rotational driving force non-transmitting state of preventing a rotational force of the roller 41 from being transmitted to the outer sheath 22, while on the other hand, the clip unit 26 reaches the target region 100, stopping the inner sheath 23 from advancing. Here, the operator stops operating the operation lever 5a.

Note that, when pulling out the sheath portion 21 as described later, operation is made to retreat the inner sheath 23 and the outer sheath 22 in this order, because of the rotational driving force non-transmitting state where the proximal end surface of the outer sheath 22 is apart from the rollers 41, 42 by the length of the contact ring 25a in that the outer sheath 22 was advanced with the distal end surface of the contact ring 25a in contact with the proximal end surface of the outer sheath 22. In other words, when retreating the inner sheath 23 with the proximal end surface of the outer sheath 22 being positioned apart from the rollers 41, 42 by the predetermined distance, it is prevented that the roller 41 contacts the outer sheath 22 thereby transmitting the rotational force of the roller 41 to the outer sheath 22, thus preventing the outer sheath 22 from being retreated together with the inner sheath 23.

Also, when the inner sheath 23 is moving relative to the outer sheath 22, the outer sheath 22 is held still without being moved as the inner sheath 23 moves, because the proximal end portion of the outer sheath 22 is in close contact with the spigot body 47 with a predetermined resistance force, and a part of the outer sheath 22 from the distal end side to a half-way portion is inserted in the treatment instrument channel 11e to be in contact with an inner circumferential surface thereof.

Figure 16:
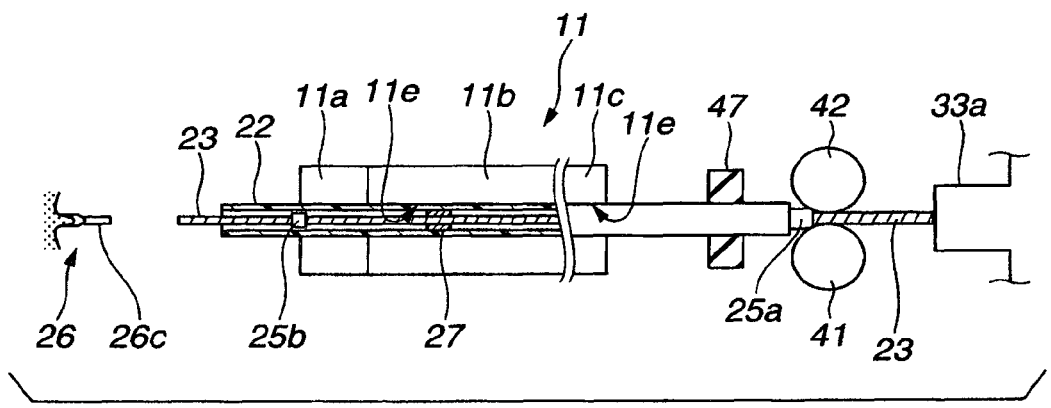
FIG. 16 is a view to illustrate a state where the clip of the clip unit is placed at the target region.

Next, the operator operates the pressing switch 5b of the operation instruction device 2. This rotates and drives the second motor 57 in a predetermined direction, moving the slider portion 54 located at the distal end side to the proximal end side, thus starting to tow the operation wire 24. As described referring to FIGS. 11, 12, the towing of the operation wire 24 results in deformation of the clip 26 to a closed state as the operation wire 24 is towed, subsequently subjecting the hook portion 26b in a J-shape to plastic deformation to an I-shape, which removes the hook portion 26b out of the loop 24b, thereby placing the clip 26a at the target region 100, as shown in FIG. 16. At this time, the proximal end surface of the contact ring 25a is supported by the rollers 41, 42 in a stopped state, thereby holding still the inner sheath 23 without the inner sheath 23 being retreated as the operation wire 24 is pulled and moved.

Next, the operator operates to incline the operation lever 5a of the operation instruction device 2 to the proximal end side, to pull the sheath portion 21 out of the treatment instrument channel 11e and house the outer sheath 22 and the inner sheath 23 in the sheath housing portion 32.

Figure 17:
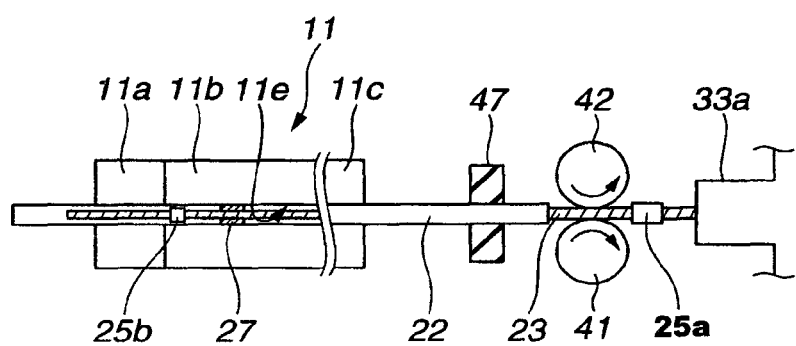
FIG. 17 is a view to illustrate a state where the rollers are reversely rotated to retreat the inner sheath.

In other words, the operator operates to incline the operation lever 5a of the operation instruction device 2 to the proximal end side, to rotate and drive the first motor 43 in a direction reverse to that mention above, to rotate the roller 41 as shown in an arrow in FIG. 17. As a result, because the proximal end surface of the outer sheath 22 is apart from the rollers 41, 42, when the roller 41 is rotated, the inner sheath 23 is retreated first, and then the contact ring 25a passes through between the rollers 41, 42, which is followed by the inner sheath 23 being again retreated with the rotation of the roller 41, to be housed in the sheath housing portion 32. At this time, as the roller 41 is rotated, the inner sheath 23 is retreated in the outer sheath 22, with the engaging ring 25b gradually approaching the stopper member 27. Also at this time, the outer sheath 22 is held still without being retreated as the inner sheath 23 is retreated, because the proximal end portion of the outer sheath 22 is in close contact with the spigot body 47 with the predetermined resistance force, and the part of the outer sheath 22 from the distal end to the half-way portion is in contact with the inner circumferential surface of the treatment instrument channel 11e.

Figure 18:
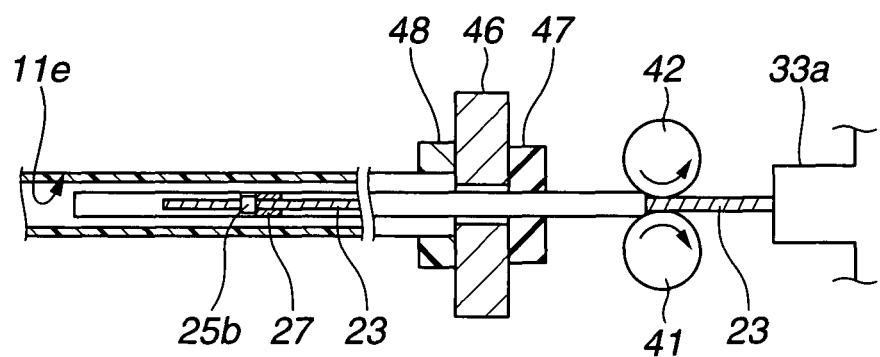
FIG. 18 is a view to illustrate a state where the outer sheath, instead of the inner sheath, is nipped by the rollers.
Figure 19:
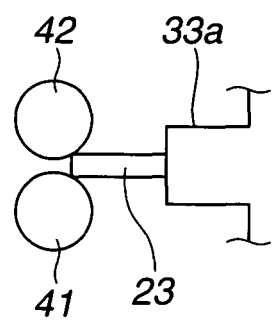
FIG. 19 is a view to illustrate a state where it is finished to pull out the sheath portion.

When the proximal end surface of the engaging ring 25b contacts the distal end surface of the stopper member 27, a retreating force is transmitted to the outer sheath 22, to integrally retreat the outer sheath 22 as the inner sheath 22 is retreated. Subsequently, instead of the inner sheath 23, the outer sheath 22 is nipped between the rollers 41, 42 as shown in FIG. 18, thereby retreating the outer sheath 22 as the roller 41 is rotated, and housing in the sheath housing portion 32 the outer sheath 22 in which the inner sheath 23 is inserted, so that the outer sheath 22 is pulled out of the treatment instrument channel 11e. After this, with the passage of the distal end of the outer sheath 22 through between the rollers 41, 42 as shown in FIG. 19, it is completed to house the sheaths 23, 22 into the sheath housing portion 32. Here, the operator stops operating the operation lever 5a.

In this manner, it is possible to control the advancing/retreating of the outer and inner sheaths configuring the sheath portion by means of the rotation of the pair of rollers, by providing the stopper member on the inner circumferential surface of the distal end portion of the outer sheath; providing the positioning member and the moving distance setting member on the outer circumferential surface of the inner sheath; configuring the sheath portion by inserting the inner sheath into the outer sheath so that the proximal end surface of the positioning member contacts the distal end surface of the stopper member and that the distal end surface of the moving distance setting member contacts the proximal end surface of the outer sheath; and providing the inserting/pulling-out device with a pair of rollers each configured with the elastic resin member, so that the sheath portion is nipped between the rollers.

Also, by providing the spigot body that closely contact the outer surface of the outer sheath and applies the outer sheath with a predetermined resistance force, near the rollers provided to the inserting/pulling-out device, in a state where the rollers are being rotated to insert the sheath portion into the treatment instrument insertion channel of the endoscope, when the distal end surface of the moving distance setting member contacts the proximal end surface of the outer sheath and the inner sheath, instead of the outer sheath, is nipped between the rollers to be moved with the rotation thereof, the outer sheath is stably held still because the proximal end portion of the outer sheath is held by the spigot body and the part of the outer sheath from the distal end side to the half-way portion is in close contact with the treatment instrument channel.

Further, by setting as required the length dimension of the moving distance setting member also serving as the rotational driving force non-transmitting member, so that, when the distal end surface of the moving distance setting member contacts the proximal end surface of the outer sheath, the proximal end surface of the outer surface is positioned away from the rollers by the length dimension of the moving distance setting member, it can be prevented that the outer sheath is rolled into the rollers when the inner sheath is moved to pull out the sheath portion.

Note that, in the present embodiment, the sheath portion 21 is pressed and nipped by the pair of rollers 41, 42. However, the member to press and nip the sheath portion 21 is not limited to the pair of rollers 41, 42, and may be the roller 41 and another member such as a block body or the like having a plane surface, for example.

Moreover, in the present embodiment, the treatment instrument is provided as the clip device 20A. However, the treatment instrument is not limited to the clip device, and may be, for example, a calculus fragmenting device 20B wherein the distal end portion of the outer sheath 22 includes a basket portion serving as a calculus fragmenting tool disposed instead of the clip unit 26. Referring to FIGS. 20 to 30, there will be described below configuration and actions of the calculus fragmenting device 20B having a different configuration of the distal end portion of the sheath portion from that of the clip device 20A.

First, referring to FIGS. 20, 21, configuration of the calculus fragmenting device 20B will be described.

In the calculus fragmenting device 20B, the sheath portion 21 is configured to include the outer sheath 22 and the inner sheath 23.

Figure 20:
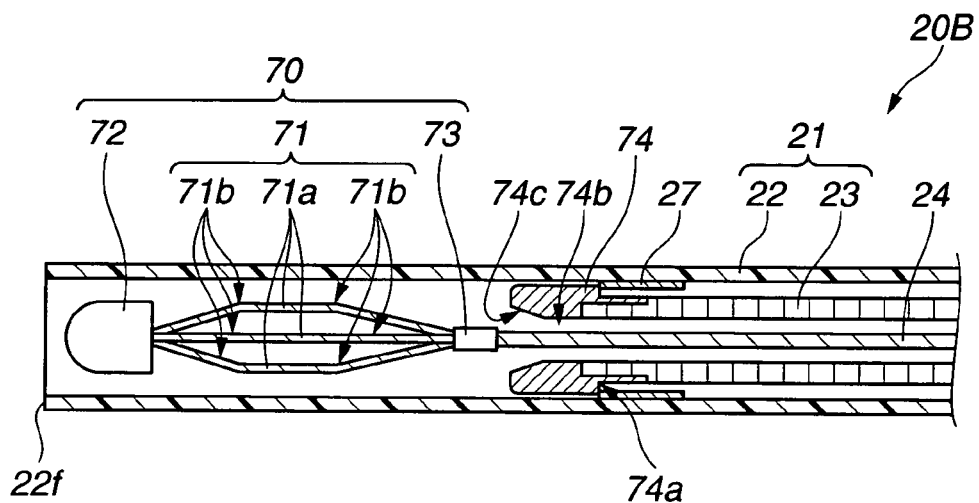
FIG. 20 is a cross sectional view to illustrate a configuration of a distal end portion of a calculus fragmenting device.
Figure 21:
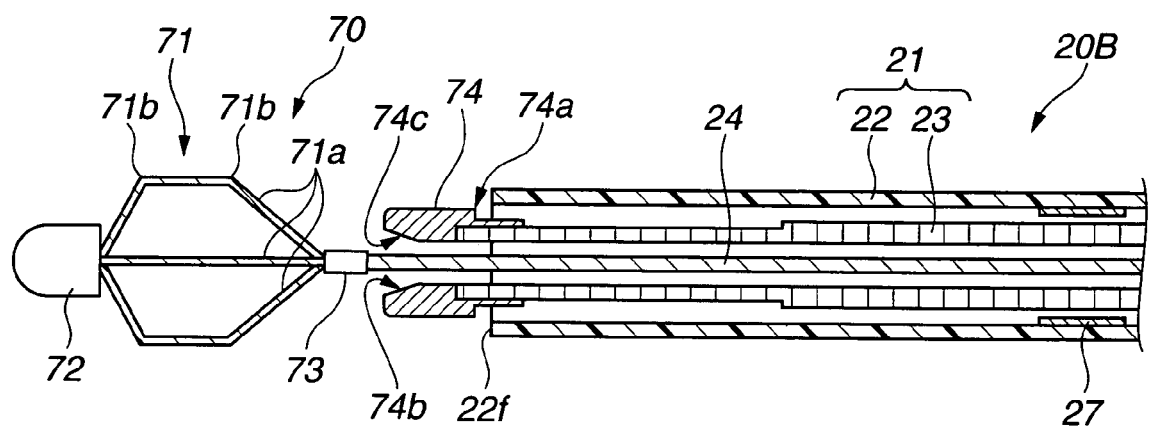
FIG. 21 is a cross sectional view to illustrate the distal end portion of the calculus fragmenting device in a state where a fragmenting tool is protruded from the outer sheath.

As shown in FIG. 20, in the distal end portion of the outer sheath 22, a fragmenting tool 70 is disposed. The fragmenting tool 70 is configured to include a basket portion 71 serving as a function portion configured by a plurality of elastic wires 71a, a distal end chip (hereinafter described as chip) 72, and a wire binding member (hereinafter described as binding member) 73. The chip 72 binds the distal ends of the plurality of elastic wires 71a. The chip 72 has a distal end portion that comes into contact with bio-tissues and is therefore formed in a shape with a curved surface. The binding member 73 is fixed to the distal end of the operation wire 24 and binds proximal ends of the plurality of elastic wires 71a.

In the present embodiment, a ring member 74 serving both as an engaging member and a fragmented calculus receiving portion is integrally fixed to the distal end of the inner sheath 23 by soldering, welding, or adhesion. On the other hand, provided at a predetermined position on the inner circumferential surface of the outer sheath 22 is the stopper member 27 with a distal end surface contacted by contact surface 74a of the ring member 74.

Further, in a state where the ring member 74 is in contact with the stopper member 27, the fragmenting tool 70 is located at the distal end of the inner sheath 23 and inside of a distal end portion of the outer sheath 22 near the distal end surface 22f, as shown in FIG. 20. That is, the ring member 74 is an advancing/retreating movement switching mechanism portion, and is a positioning member to set the position of the distal end portion of the inner sheath 23 in the distal end portion of the outer sheath 22.

Note that the elastic wires 71a are equipped with a plurality of inflecting portions 71b. When the inner sheath 23 is advanced relative to the outer sheath 22 as shown in FIG. 21, the fragmenting tool 70 located in the distal end portion of the outer sheath 22 as shown in FIG. 20 is protruded from the distal end surface 22f of the outer sheath 22 to expand the basket portion 71.

In a state where a calculus, for example, is taken in the basket portion 71 expanded, the operation wire 24 is towed toward the hand side by a predetermined amount. Then, along with the movement of the operation wire 24 toward the hand side, the binding member 73 and the elastic wires 71a are pulled into a penetrating hole 74b provided to the ring member 74, gradually reducing the diameter of the basket portion 71 expanded, thus constricting the calculus. By further towing the operation wire 24 to reduce the diameter of the basket portion 71, the elastic wires 71a fractures the calculus, and a proximal end surface 72r of the chip 72 contacts a distal end surface of the ring member 74.

On a distal end surface side of the penetrating hole 74b of the ring member 74 is provided a taper surface 74c having an aperture diameter gradually reducing from the distal end side to the half-way portion of the ring member 74. This causes the diameter of the expanded basket portion 71 to be gradually reduced from the proximal end side.

Other components are the same as those of the clip device 20A and are attached with the same reference symbols, the descriptions thereof being omitted. The sheath portion 21 of the calculus fragmenting device 20B is housed in the sheath housing portion 32 of the case main body 31, similarly with the clip device 20A described above.

Next, referring to FIGS. 22 to 30, there will be described actions when the calculus fragmenting device 20B configured as above is attached to the treatment instrument mounting portion 8b of the electric operation device 8.

First, in performing an operation, a staff connects the wire connector 24a to the operation wire fixing portion 56 as mentioned above, and then locates the case main body 31 at a predetermined position of the treatment instrument mounting portion 8b and the extension portion connector 36a to the extension portion fixing portion 53. The staff also mounts the spigot body 47 compatible with the outer sheath 22 to the attachment board 46 equipped to the inserting/pulling-out device 40, and also mounts the connection tube 9, of which one end portion is connected to the treatment instrument lead-in port 12b, to the tube attaching portion 48 by the other end portion. Furthermore, the staff electrically connects the signal cable 2a of the operation instruction device 2 to the control device 7, and electrically connects the control device 7 and the electric operation device 8 with the signal cable 7b.

Figure 22:
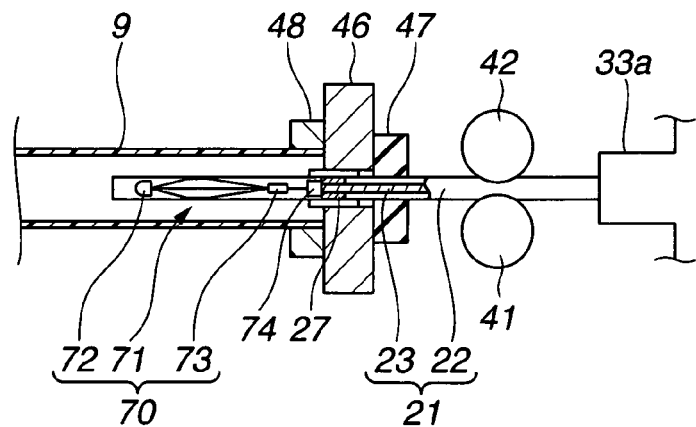
FIG. 22 is a view to illustrate a state where an outer sheath of the calculus fragmenting device is nipped by the rollers.

The staff next locates in the connection tube 9 the outer sheath 22 exposed from the distal end surface of the sheath lead-out portion 33a, via between the opened rollers 41, 42, and through the spigot body 47, the attachment board 46, and the tube attaching portion 48. Subsequently, the staff locates the opening/closing lever 49 as shown in the solid line, so that the outer sheath 22 is nipped between the rollers 41, 42 as shown in FIG. 22. This completes the pre-operation preparation.

Endoscopic observation is performed to confront the distal end portion 11a of the endoscope 10 with, for example, a duodenal papilla not shown. Then, in using the calculus fragmenting device 20B, the operator operates to incline the operation lever 5a of the operation instruction device 2 toward the distal end side, to lead the sheath portion 21 into, for example, a bile duct (not shown).

Figure 23:
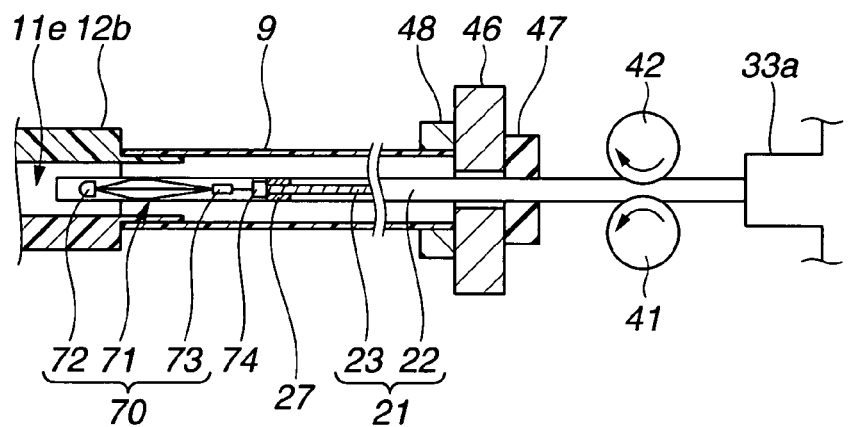
FIG. 23 is a view to illustrate a state where the outer sheath of the calculus fragmenting device is being advanced by the rollers.

When the operator operates to incline the operation lever 5a, the first motor 43 is rotated and driven in a predetermined direction, thus starting to rotate the roller 41 as shown in an arrow in FIG. 23. The rotation of the roller 41 causes the outer sheath 22 to be advanced along with the rotation of the roller 41, against the urging force of the spigot body 47. The advancement of the outer sheath 22 causes the distal end surface of the stopper member 27 to contact the proximal end surface of the ring member 74, thus integrally advancing the inner sheath 23 and the outer sheath 22. The outer sheath 22 and the inner sheath 23 pass through the treatment instrument lead-in port 12b provided to the operation portion 12 of the endoscope 10, to be inserted and subsequently advanced in the treatment instrument channel 11e.

Figure 24:
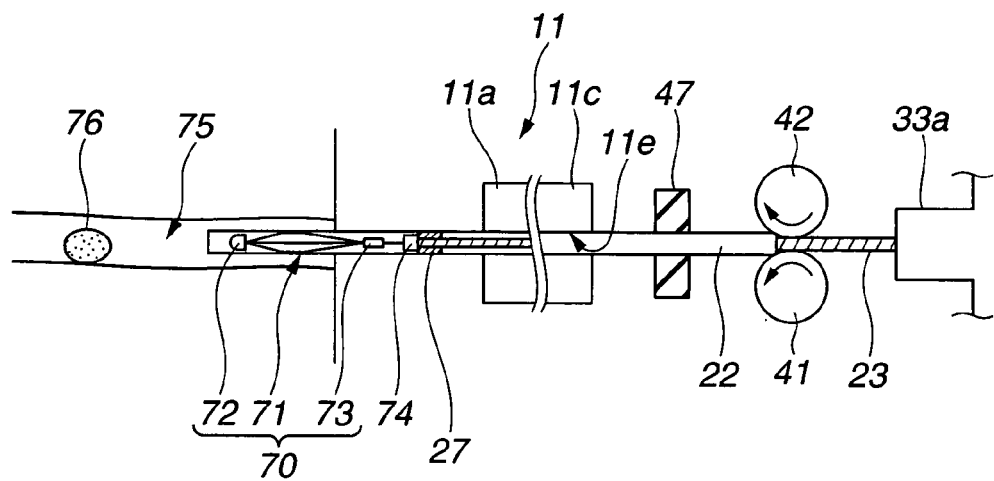
FIG. 24 is a view to illustrate a state where the inner sheath, instead of the outer sheath, is nipped by the rollers.

After the distal end portion of the outer sheath 22 advancing in the treatment instrument channel 11e is led out from the distal end surface of the distal end portion 11a as shown in FIG. 24, the outer sheath 22 is in a state of having been led into the bile duct 75, with the inner sheath 23, instead of the outer sheath 22, nipped between the rollers 41, 42.

Figure 25:
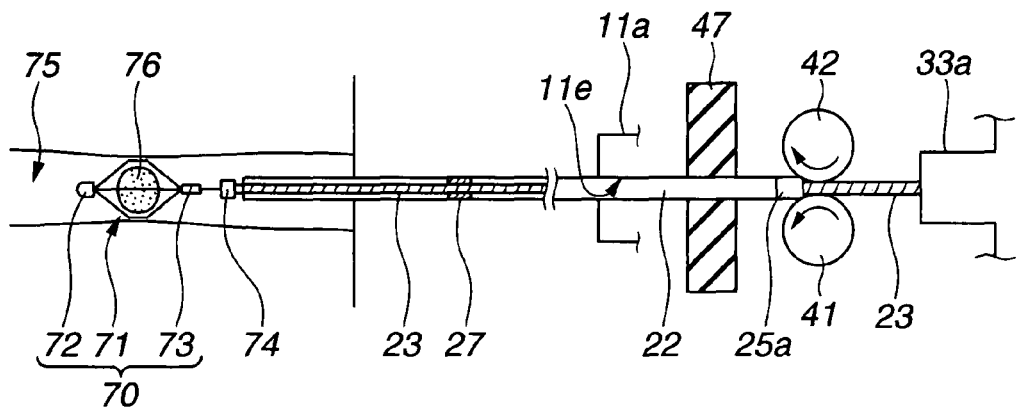
FIG. 25 is a view to illustrate a state where the inner sheath is advanced by the rollers to expand a basket portion of the fragmenting tool so as to take in a calculus therein.

Then, the inner sheath 23 is advanced in the outer sheath 22 along with the rotation of the roller 41, protruding the fragmenting tool 70 from the outer sheath 22 to expand the basket portion 71. The contact ring 25a passes through between the rollers 41, 42 as shown in FIG. 25, causing the distal end surface of the contact ring 25a to contact the proximal end surface of the outer sheath 22, thus placing the proximal end surface of the outer sheath 22 apart from the rollers 41, 42 by the length of the contact ring 25a, which results in the state of non-transmission of rotational driving force. At this time, the fragmenting tool 70 reaches near a calculus 76, stopping the inner sheath 23 from advancing. Here, the operator stops operating the operation lever 5a.

Figure 26:
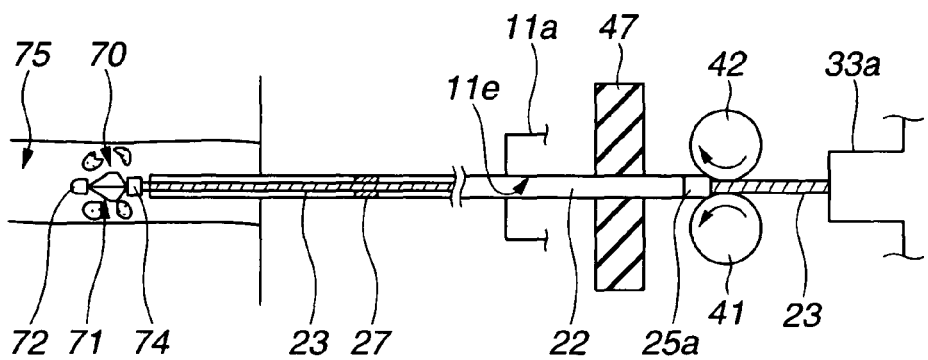
FIG. 26 is a view to illustrate a state where the calculus taken in the basket portion is fragmented.
Figure 27:
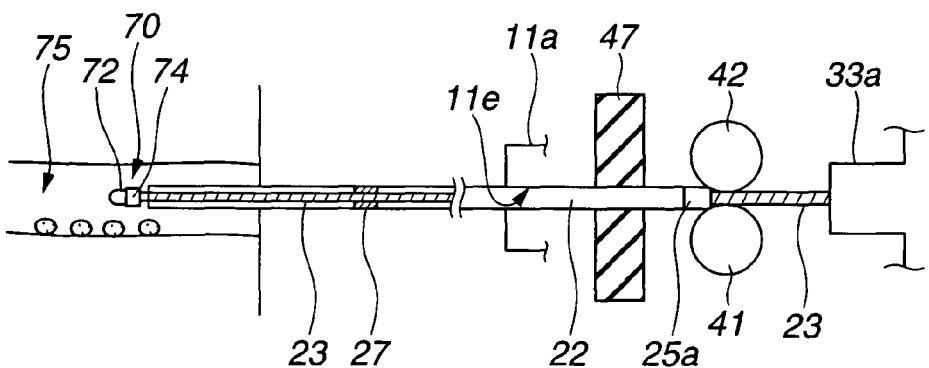
FIG. 27 is a view to illustrate a state where it is finished to fragment the calculus.

Next, the operator operates the pressing switch 5b of the operation instruction device 2, to rotate and drive the second motor 57 in a predetermined direction, moving the slider portion 54 located on the distal end side to the proximal end side, thus towing the operation wire 24. The tow of the operation wire 24 results in gradual decrease of the diameter of the basket portion 71 along with the tow of the operation wire 24, from the expanded state of the basket portion 71. If, at this time, the calculus 76 is taken in the basket portion 71 expanded, the calculus 76 is fractured as shown in FIG. 26 by the elastic wires 71a of the basket portion 71 which is reduced in diameter as the operation wire 24 is towed. At this time, the inner sheath 23 is held still without being retreated as the operation wire 24 is towed and moved, because the proximal end surface of the contact ring 25a is supported by the rollers 41, 42 stopped. By further continuing the tow of the operation wire 24, the proximal end surface of the chip 72 is caused to contact the distal end surface of the ring member 74 as shown in FIG. 27, therewith completing the fracturing of the calculus 76.

Next, the operator operates to incline the operation lever 5a of the operation instruction device 2 to the proximal end side, to pull out the sheath portion 21 from the treatment instrument channel 11e and house the inner sheath 23 and the outer sheath 22 in the sheath housing portion 32.

Figure 28:
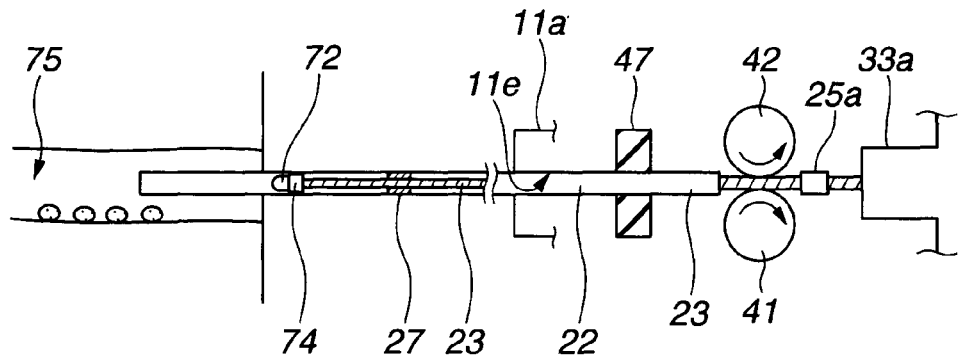
FIG. 28 is a view to illustrate a state where the rollers are reversely rotated to retreat the inner sheath.

That is, the operator operates to incline the operation lever 5a to the proximal end side to rotate and drive the first motor 43 in a direction reverse to that mentioned above, to rotate the roller 41 as shown in the arrow in FIG. 28. As a result, because the proximal end surface of the outer sheath 22 is apart from the rollers 41, 42, when the roller 41 is rotated, first the inner sheath 23 is retreated, and then the contact ring 25a passes through between the rollers 41, 42, which is followed by the inner sheath 23 being retreated again with the rotation of the roller 41 and housed in the sheath housing portion 32. At this time, as the roller 41 is rotated, the inner sheath 23 is retreated in the outer sheath 22, with the ring member 74 gradually approaching the stopper member 27.

Figure 29:
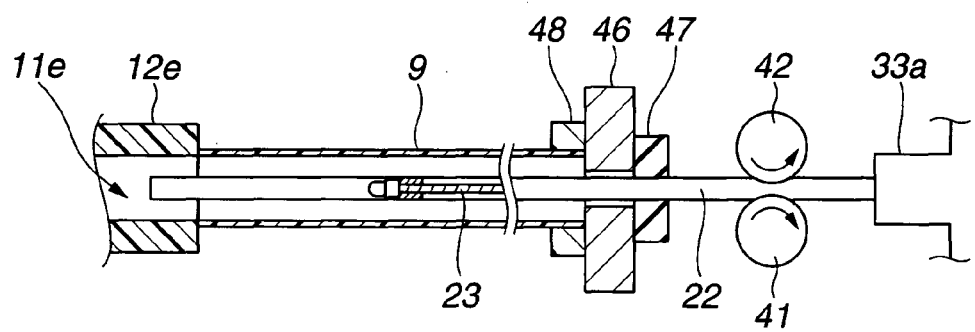
FIG. 29 is a view to illustrate a state where the outer sheath is being retreated by the rollers.
Figure 30:
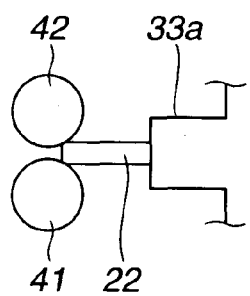
FIG. 30 is a view to illustrate a state where it is finished to pull out the sheath portion.

With the proximal end surface of the ring member 74 coming into contact with the distal end surface of the stopper member 27, the inner sheath 23 and the outer sheath 22 are integrally retreated. Subsequently, instead of the inner sheath 23, the outer sheath 22 is nipped between the rollers 41, 42 thereby retreating the outer sheath 22 as the roller 41 is rotated as shown in FIG. 29, to house the outer sheath 22 in which is inserted the inner sheath 23 in the sheath housing portion 32 and pull the outer sheath 22 out of the treatment instrument channel 11e. After this, with the passage of the distal end of the outer sheath 22 through between the rollers 41, 42 as shown in FIG. 30, it is completed to house the sheaths 23, 22 into the sheath housing portion 32. Here, the operator stops operating the operation lever 5a.

The similar actions and effects can be obtained also with the clip device. Referring to FIGS. 31 to 47, a second embodiment of the present invention will be described.

First, referring to FIGS. 31 to 33, configuration of an endoscope system of the present embodiment will be described.

Figure 31:
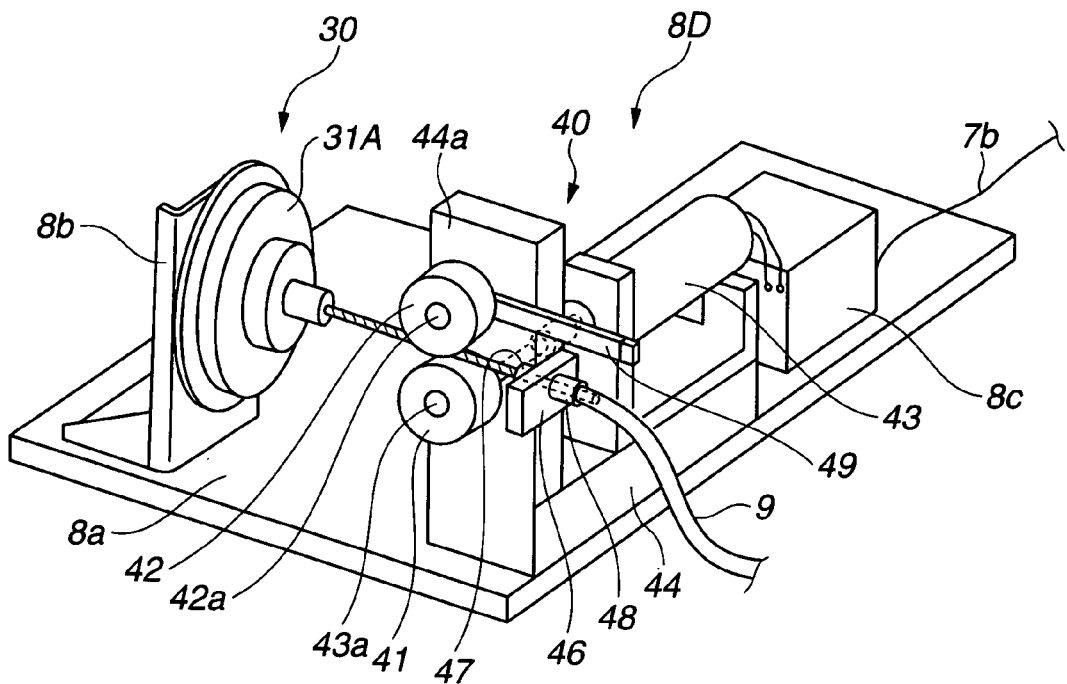
FIG. 31 is a view to illustrate an exemplary configuration of the electric operation device including only an inserting/pulling-out device.

The endoscope system as a medical apparatus of the present embodiment is configured so that an electric operation device 8D includes only the inserting/pulling-out device 40, without providing the activating device 50, as shown in FIG. 31. A case main body 31A to be mounted to the treatment instrument mounting portion 8b included in the electric operation device 8D is configured to include the first member 33 and a second member 80, as shown in FIG. 32. Unlike the second member 34 in the first embodiment, the second member 80 does not include the sheath proximal-end fixing portion 35.

Figure 33:
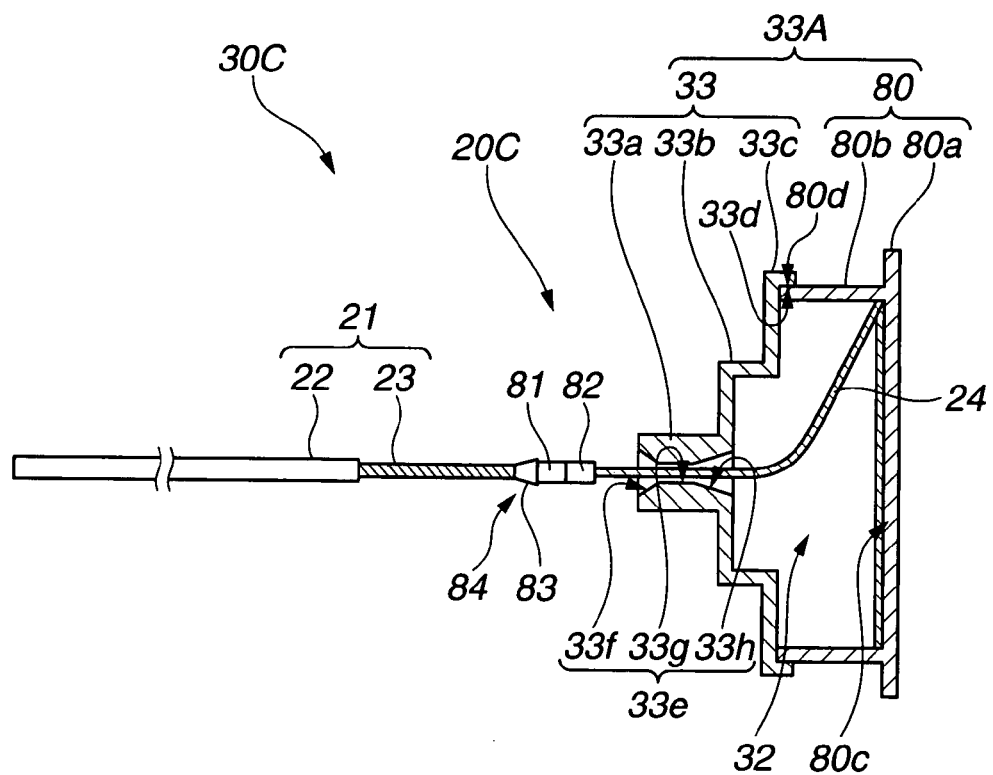
FIG. 33 is a view to illustrate a configuration of the sheath portion configured by the outer sheath, the inner sheath, and an operation wire disposed in the case main body.

As shown in FIG. 33, of the outer sheath 22, the inner sheath 23, and the operation wire 24 housed in the sheath housing portion 32 of the case main body 31A, the operation wire 24 has a proximal end portion that is integrally fixed to a bottom surface 80c of a space configured by a plane portion 80*a* and an annular portion 80*b* configuring the second member 80, by a fixing tool not shown provided to the bottom surface 80*c*.

Note that the first member 33 and the second member 80 are configured to be integrally connected with screwing similarly as mentioned above. Also, at least one of the members 33, 80 configuring the case main body 31A is configured with a transparent or semi-transparent resin member similarly as mentioned above. Reference symbol 80*d* designates a male screw to be screwed to the female screw 33*d* of the first member 33.

In the endoscope system of the present embodiment, with rotations of the rollers 41, 42 are performed advancing/retreating of the outer sheath 22 and the inner sheath 23, as well as the towing operation of the operation wire 24. To this end, a clip device 20C is configured as described below.

Figure 32:
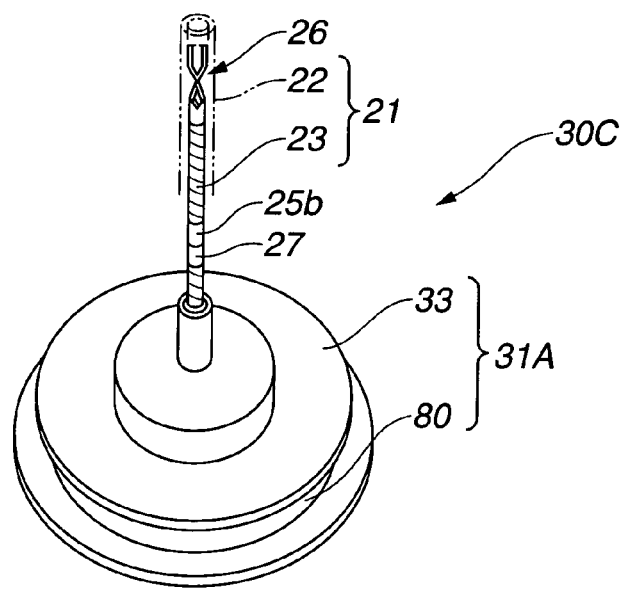
FIG. 32 is a view to illustrate the clip device cartridge wherein a case main body in a different configuration includes a clip device in another configuration.

In the present embodiment, the treatment instrument 20 is provides as a clip device 20C, and the treatment instrument cartridge is provided as a clip device cartridge 30C wherein the sheath portion 21 of the clip device 20C is housed in the sheath housing portion 32 of the case main body 31A as shown in FIGS. 32, 33.

Figure 34:
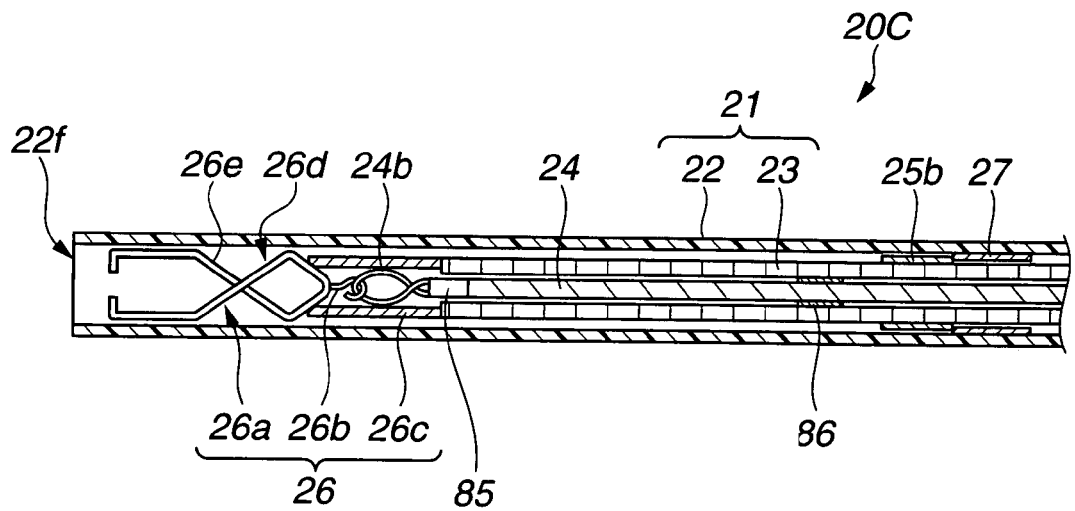
FIG. 34 is a cross sectional view to illustrate characteristics of a distal end portion of a clip device in another configuration.

Referring to FIGS. 33, 34, the clip device 20C included in the clip device cartridge 30C will be described.

As shown in FIG. 33, the clip device 20C includes the sheath portion 21 to be housed in the sheath housing portion 32 of the case main body 31A. The sheath portion 21 is configured to include the outer sheath 22 which is an exterior member, the inner sheath 23 which is an insertion member having a hollow portion, and the operation wire 24 which is an insertion member with a small diameter. In the present embodiment, the operation wire 24 is slidably located in the hollow portion of the inner sheath 23, and the proximal end side of the operation wire 24 is extended from the proximal end surface of the inner sheath 23 in the sheath housing portion 32.

To the proximal end portion of the inner sheath 23 extending from the proximal end surface of the outer sheath 22 is fixed a holding member 81 which is an advancing/retreating movement switching mechanism portion. The holding member 81 is a stepped tubular member, having a distal end portion 83 with a large diameter including a taper portion 84. The taper portion 84 is configured to be engageable with the proximal end portion of the outer sheath 22.

On the other hand, at a half-way portion of the operation wire 24, there is fixed a second contact ring 82 which is an advancing/retreating movement switching mechanism portion for setting a movement distance of the clip unit 26, similarly with the contact ring 25*a*. The second contact ring 82 is located at a position such that, in a state where the distal end surface of the second contact ring 82 is in contact with the proximal end surface of the holding member 81, the clip unit 26 is housed in the distal end portion of the outer sheath 22, as shown in FIG. 34 to be described later.

As shown in FIG. 34, in the present embodiment, in addition to the engaging ring 25*b* fixed at a predetermined position on the distal end side of the inner sheath 23, and the stopper member 27 fixed at a predetermined position on the distal end side of the outer sheath 22, there are provided a wire engaging portion 85 which is a second engaging member with respect to the engaging ring 25*b*, and a wire stopper 86 which is a second stopper member with respect to the stopper member 27. The wire stopper 86 is an advancing/retreating movement switching mechanism portion, and is fixed on an inner circumferential surface at a predetermined position on the distal end side of the inner sheath 23. The wire engaging portion 85 is an advancing/retreating movement switching mechanism portion, and is integrally fixed to a proximal end of the loop 24*b* which is the distal end portion of the operation wire 24.

The wire stopper 86 is a wire movement restricting member to restrict the wire engaging portion 85 from moving toward the proximal end side than the wire stopper 86, and is so configured that the proximal end surface of the wire engaging portion 85 contact a distal end surface of the wire stopper 86.

Other components are the same as those in the first embodiment, and the same members are attached with the same reference symbols, the descriptions thereof being omitted.

Referring to FIGS. 35 to 47, there will be described actions of the endoscope system 1 wherein the clip device cartridge 30C configured as mentioned above is attached to the treatment instrument mounting portion 8*b*.

First, in performing an operation, a staff locates the case main body 31A at a predetermined position of the treatment instrument mounting portion 8*b*. The staff also mounts the spigot body 47 compatible with the outer sheath 22 to the attachment board 46 included in the inserting/pulling-out device 40, and also mounts the connection tube 9, of which one end portion is connected to the treatment instrument lead-in port 12*b*, to the tube attaching portion 48 by the other end portion. Further, the staff electrically connects the signal cable 2*a* of the operation instruction device 2 to the control device 7, and also electrically connects the control device 7 and the electric operation device 8D with the signal cable 7*b*.

Figure 35:
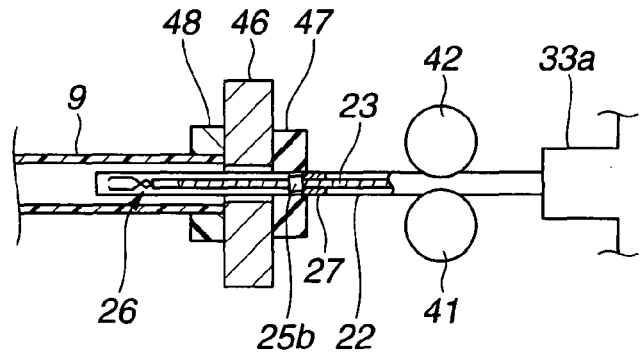
FIG. 35 is a view to illustrate a state where the outer sheath of the clip device is nipped by the rollers.

Next, the staff locates in the connection tube 9 the outer sheath 22 exposed from the distal end surface of the sheath lead-out portion 33*a*, via between the rollers 41, 42 in an opened state, and through the spigot body 47, the attachment board 46, and the tube attaching portion 48. Then, the staff locates the opening/closing lever 49 as shown in the solid line, so that the outer sheath 22 is nipped between the rollers 41, 42, as shown in FIG. 35. This completes the pre-operation preparation.

When using the clip device 20C after specifying a target region by performing endoscopic observation, the operator operates to incline the operation lever 5*a* of the operation instruction device 2 toward the distal end side, to lead the sheath portion 21 into the body cavity.

Figure 36:
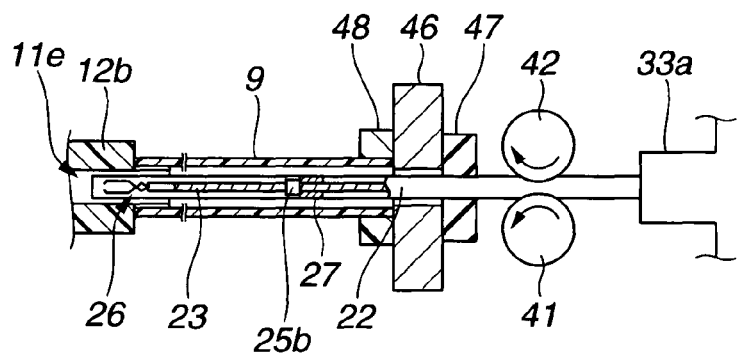
FIG. 36 is a view to illustrate a state where the outer sheath of the clip device is being advanced by the rollers.

The operator operates the operation lever 5*a* to rotate and drive the first motor 43 in a predetermined direction, causing the roller 41 to rotate as shown in an arrow in FIG. 36. Then, the outer sheath 22 and the inner sheath 23 are integrally advanced along with the rotation of the roller 41. Subsequently, the outer sheath 22 and the inner sheath 23 pass through the treatment instrument lead-in port 12*b* provided to the operation portion 12 of the endoscope 10, to be inserted and subsequently advanced in the treatment instrument channel 11*e*.

Figure 37:
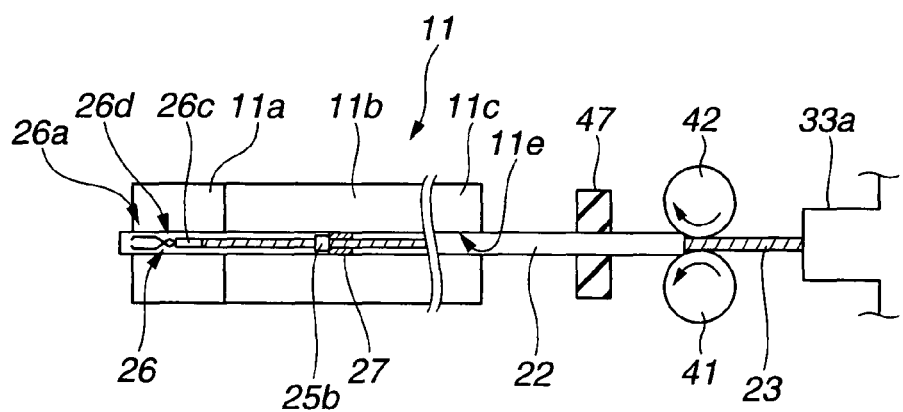
FIG. 37 is a view to illustrate a state where the inner sheath, instead of the outer sheath, is nipped by the rollers.

The distal end portion of the outer sheath 22 advancing in the treatment instrument channel 11*e* is led out into the body cavity from the distal end surface of the distal end portion 11*a*, as shown in FIG. 37. Almost simultaneously with the distal end portion of the outer sheath 22 being led out, the inner sheath 23, instead of the outer sheath 22, is nipped between the rollers 41, 42.

Figure 38:
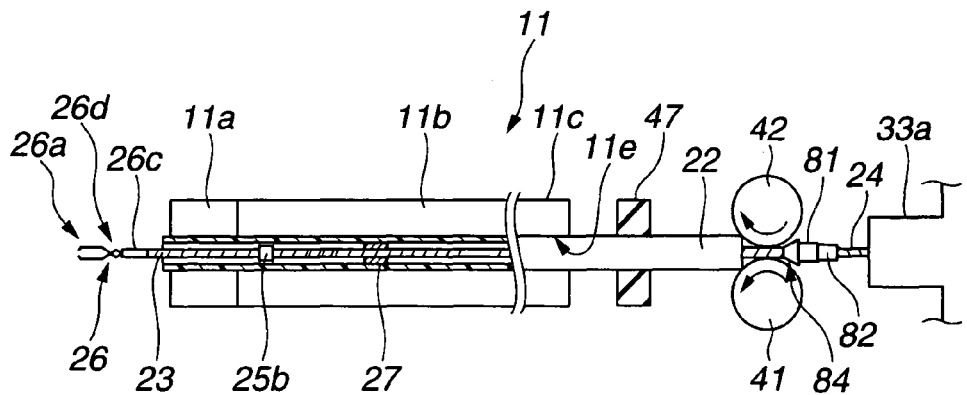
FIG. 38 is a view to illustrate a state where the inner sheath is advanced by the rollers to protrude the clip unit from the outer sheath, so that a taper portion of a holding member has reached the rollers.
Figure 39:
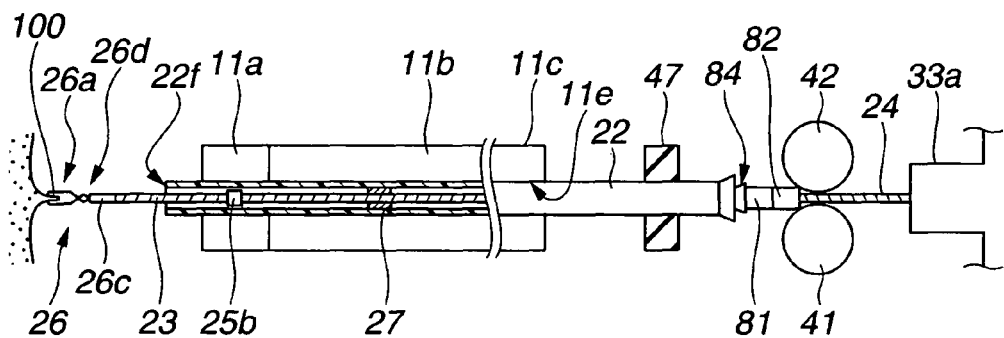
FIG. 39 is a view to illustrate a state where the holding member and a second contact ring have passed through the rollers.
Figure 40:
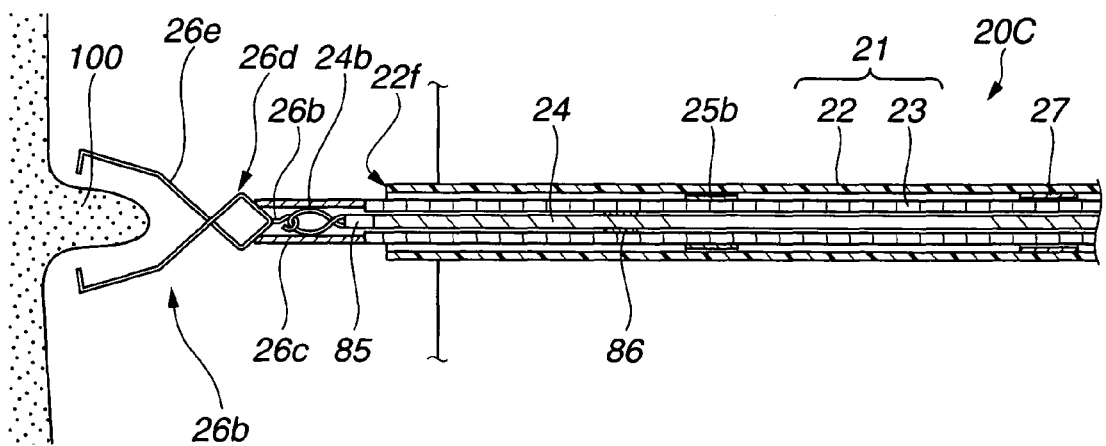
FIG. 40 is a view to illustrate a state where the clip of the clip unit is protruded from the outer sheath and located at the target region.

This causes the inner sheath 23 to advance in the outer sheath 22 as the roller 41 rotates, protruding the clip unit 26 from the distal end surface 22*f* of the outer sheath 22 as shown in FIG. 38, followed by the inner sheath 22 also being led out into the body cavity. At this time, the taper portion 84 of the holding member 81 provided at the proximal end of the inner sheath 22 is located between the rollers 41, 42, which is followed by the holding member 81 and the second contact ring 82 sequentially passing through between the rollers 41, 42, resulting in a rotational driving force non-transmitting state, as shown in FIG. 39. Then, the taper portion 84 of the holding member 81 is engaged in the proximal end portion of the outer sheath 22, with the outer sheath 22 being advanced to be apart from the rollers 41, 42 by the lengths of the holding member 81 and the second contact ring 82, and the clip unit 26 reaches the target region 100 as shown in FIG. 40. Here, the operator pauses the operation of the operation lever 5a.

Figure 41:
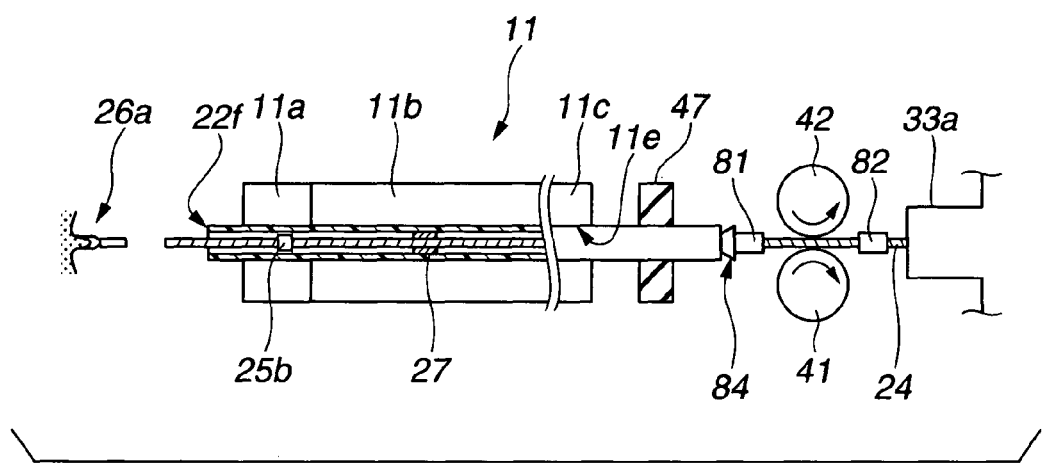
FIG. 41 is a view to illustrate a state where the rollers are reversely rotated to retreat the operation wire.
Figure 42:
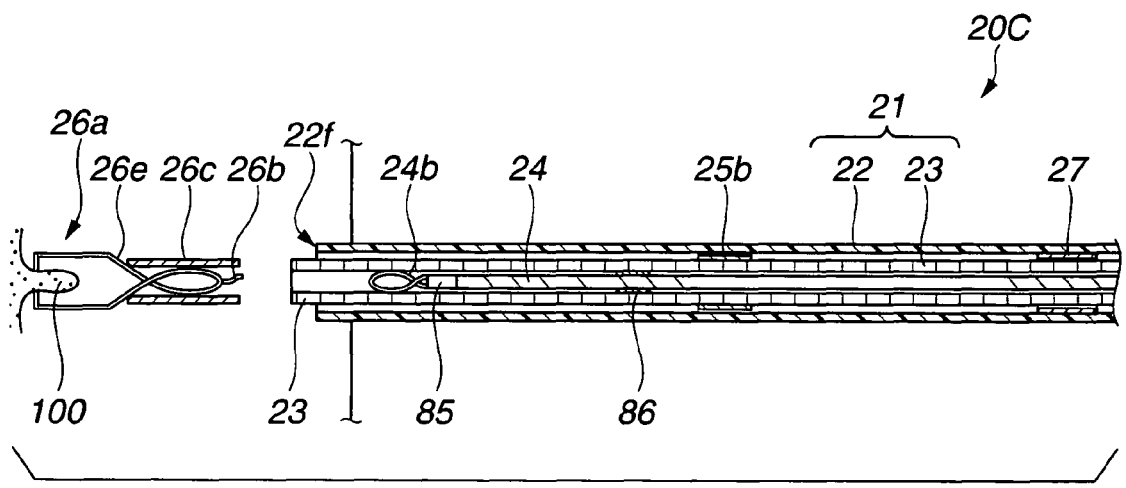
FIG. 42 is a view to illustrate a state where the clip of the clip unit is placed at the target region.

Next, the operator operates to incline the operation lever 5a to the proximal end side, to cause the first motor 43 to rotate in a direction reverse to that mention above, rotating the roller 41 as shown in an arrow in FIG. 41. This results in that the operation wire 24 is located between the rollers 41, 42, and that the proximal end surface of the inner sheath 23 and the proximal end surface of the outer sheath 22 are apart from the rollers 41, 42. Therefore, when the roller 41 is rotated, only the operation wire 24 is towed, followed by the second contact ring 82 passing through between the rollers 41, 42, with the operation wire 24 being again retreated along with the rotation of the roller 41 and thus housed in the sheath housing portion 32.

With the towing of the operation wire 24, the clip 26a is deformed into a closed state as mentioned above as shown in FIG. 42, and then the hook portion 26b in a J-shape is subject to plastic deformation to an I-shape, removing the hook portion 26b from the loop 24b, to place the clip 26a at the target region 100. At this time, because the operation wire 24 is retreated with the rotation of the rollers 41, 42, the wire engaging portion 85 provided to the distal end portion of the operation wire 24 is retreated toward the wire stopper 86 provided to the inner sheath 23.

Figure 43:
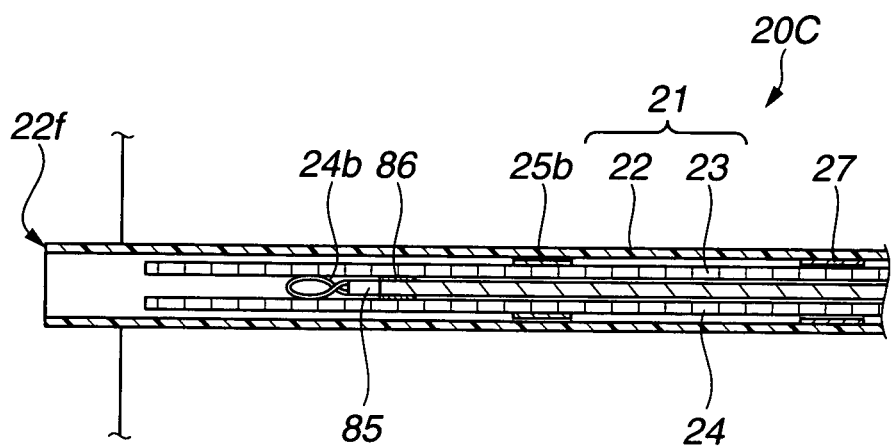
FIG. 43 is a view to illustrate a state where a wire engaging portion comes in contact with a wire stopper, so that the operation wire retreats the inner sheath.

Further, with the operation wire 24 being retreated with the rotation of the rollers 41, 42, the proximal end surface of the wire engaging portion 85 comes into contact with the distal end surface of the wire stopper 86. After this, along with the tow of the operation wire 24, the inner sheath 23 protruded from the distal end surface of the endoscope is retreated in the outer sheath 22 integrally with the operation wire 24 toward the proximal end side, as shown in FIG. 43.

Figure 44:
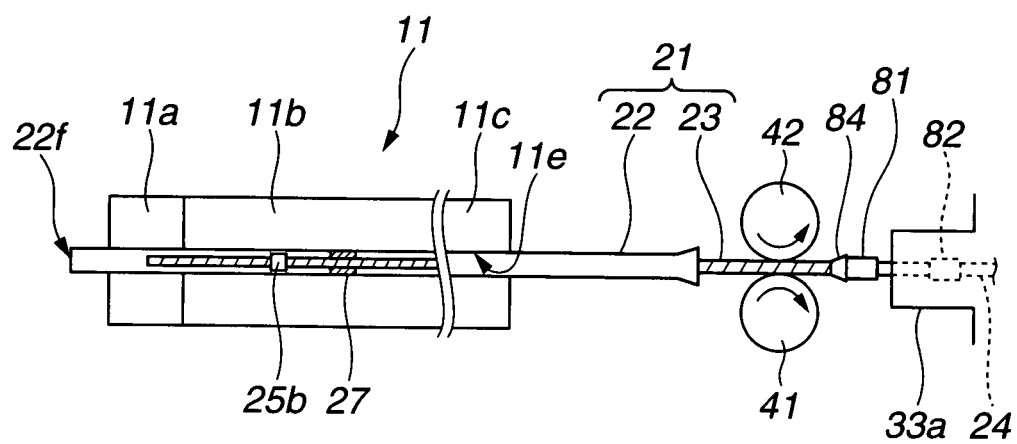
FIG. 44 is a view to illustrate a state where the inner sheath is being retreated by the rollers.
Figure 45:
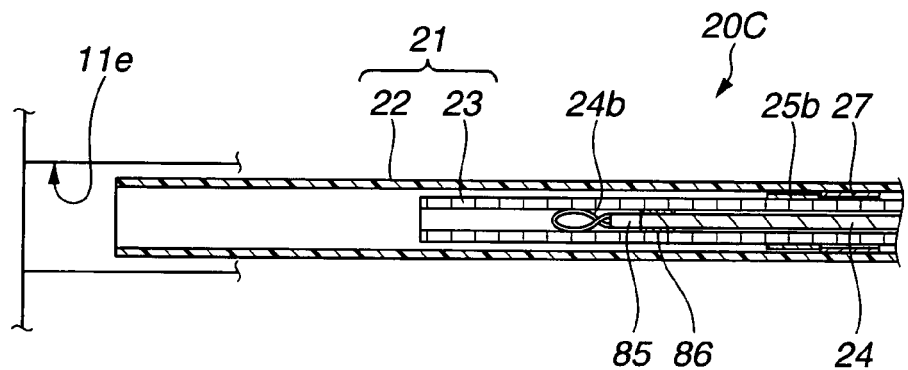
FIG. 45 is a view to illustrate a state where an engaging ring comes into contact with a stopper member, so that the inner sheath retreats the outer sheath.

As a result, the taper portion 84 of the holding member 81 engaged in the proximal end portion of the outer sheath 22 is disengaged from the proximal end surface of the outer sheath 22, followed by passage of the holding member 81 through between the rollers 41, 42, so that the inner sheath 23 is nipped between the rollers 41, 42, as shown in FIG. 44. The nipping of the inner sheath 23 between the rollers 41, 42 causes the inner sheath to retreat in the outer sheath 22 when the roller 41 is rotated, resulting in the proximal end surface of the engaging ring 25b coming into contact with the distal end surface of the stopper member 27 as shown in FIG. 45, which makes the outer sheath 22 and the inner sheath 23 integrally retreat.

Figure 46:
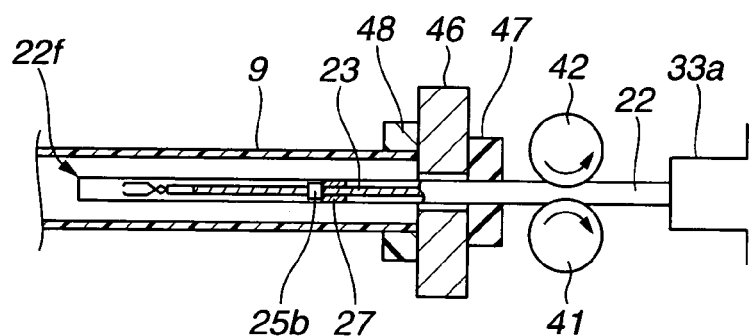
FIG. 46 is a view to illustrate a state where the outer sheath, instead of the inner sheath, is nipped by the rollers.
Figure 47:
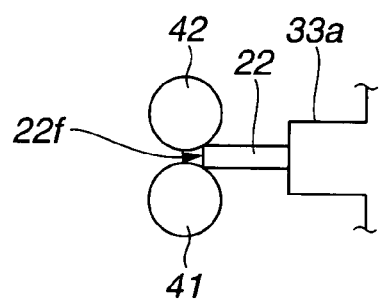
FIG. 47 is a view to illustrate a state where it is finished to pull out the sheath portion.

After this, as shown in FIG. 46, the outer sheath 22, instead of the inner sheath 23, is nipped between the rollers 41, 42, which retreats the outer sheath 22 as the roller 41 is rotated, thus housing the outer sheath 22 in the sheath housing portion 32. After the outer sheath 22 is pulled out of the treatment instrument channel 11e, passing through the connection tube 9, the distal end surface 22f of the outer sheath 22 passes through between the rollers 41, 42 as shown in FIG. 47, therewith completing housing the operation wire 24 and the outer sheaths 23, 22 into the sheath housing portion 32. Here, the operator stops operating the operation lever 5a.

In this manner, by configuring the sheath portion with the outer and inner sheaths and the operation wire, providing the outer sheath with the stopper member, providing the inner sheath with the engaging ring, the wire stopper, and the holding member, providing the operation wire with the wire engaging portion and the second contact ring, it is made possible to cause the rollers to advance/retreat the outer and inner sheaths and the operation wire as needed, to place the clip at the target region without using the activating device.

Note that, also in the endoscope system including the electric operation device 8D, the treatment instrument is not limited to the clip device 20C, and may be a calculus fragmenting device 20D disposed with a basket portion serving as a calculus fragmenting tool, instead of the clip unit 26. Referring to FIGS. 48 to 59, there will be described below configuration and effects of the calculus fragmenting device 20D including the calculus fragmenting tool.

First, referring to FIGS. 48, 49, configuration of the calculus fragmenting device 20D will be described.

Figure 48:
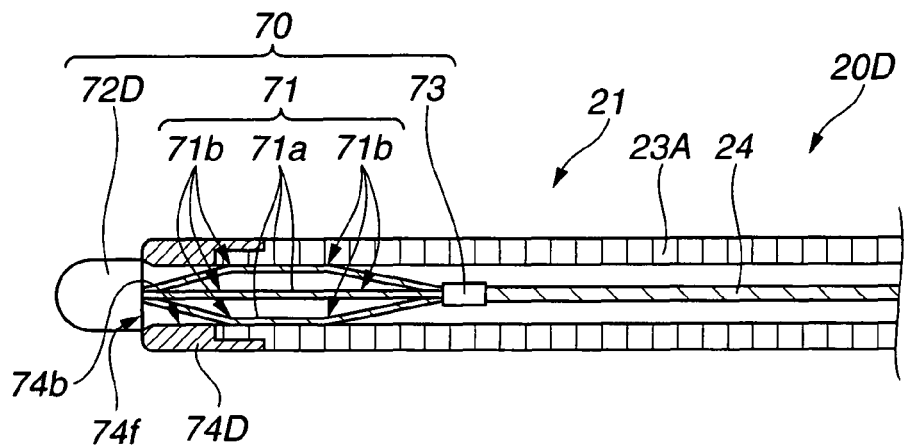
FIG. 48 is a cross sectional view to illustrate a configuration of a distal end portion of a calculus fragmenting device in another configuration.

In the calculus fragmenting device 20D, the sheath portion 21 is configured by a coil sheath 23A that was the inner sheath 23, as shown in FIG. 48.

The coil sheath 23A is an exterior member, and has a distal end portion in which is disposed a basket portion 71 and the binding member 73 that configure the fragmenting tool 70. The fragmenting tool 70 includes the basket portion 71, a chip 72D, and the binding member 73, similarly with the above-mentioned calculus fragmenting device 20B. The chip 72D is an engaging member of an advancing/retreating movement switching mechanism portion, and is located to contact a distal end surface of the ring member 74D disposed at the distal end of the coil sheath 23A.

In other words, in the present embodiment, the fragmenting tool 70 is located at the distal end portion of the coil sheath 23A, in a state where the proximal end surface 72r of the chip 72D is in contact with the distal end surface of the ring member 74D. The ring member 74D of the present embodiment is the advancing/retreating movement switching mechanism portion, and serves both as a stopper member for positioning the fragmenting tool 70 and as a fragmented calculus receiving portion.

Figure 49:
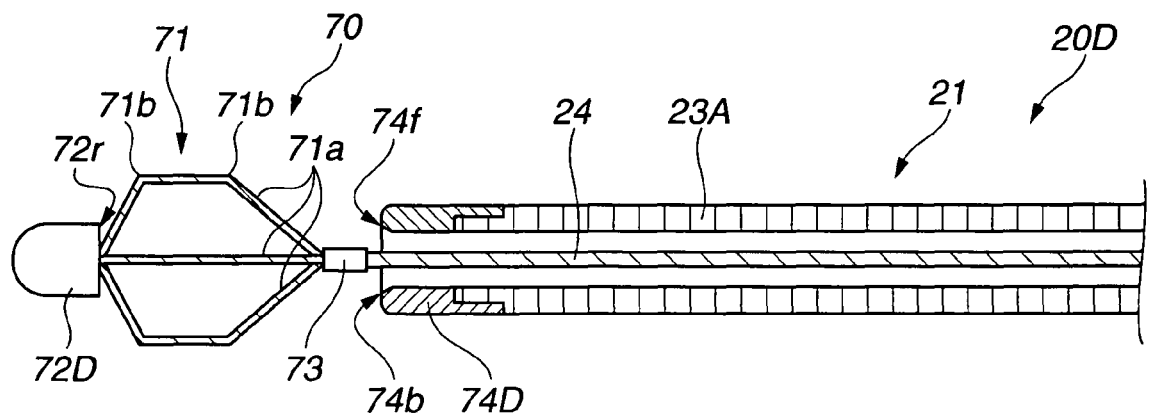
FIG. 49 is a cross sectional view to illustrate the distal end portion of the calculus fragmenting device in a state where the fragmenting tool is protruded from a coil sheath.

By advancing the operation wire 24 as an insertion member toward the distal end side, the fragmenting tool 70, wherein the basket portion 71 and the binding member 73 are housed in the distal end portion of the coil sheath 23A, and the chip 72D is located at the distal end surface of the ring member 74D, is pushed out from the distal end surface of the ring member 74D, to expand the basket portion 71 as shown in FIG. 49.

When the operation wire 24 is towed toward the hand side by a predetermined amount in a state where a calculus, for example, is taken in the expanded basket portion 71, the binding member 73 and the elastic wires 71a are pulled into the penetrating hole 74b included in the ring member 74D as the operation wire 24 is retreated, thus reducing the diameter of the expanded basket portion 71 to constrict the calculus. With further retreat of the operation wire 24 further reducing the diameter of the basket portion 71, the calculus is fractured by the elastic wires 71a, causing the proximal end surface 72r of the chip 72D to contact the distal end surface of the ring member 74D.

Figure 50:
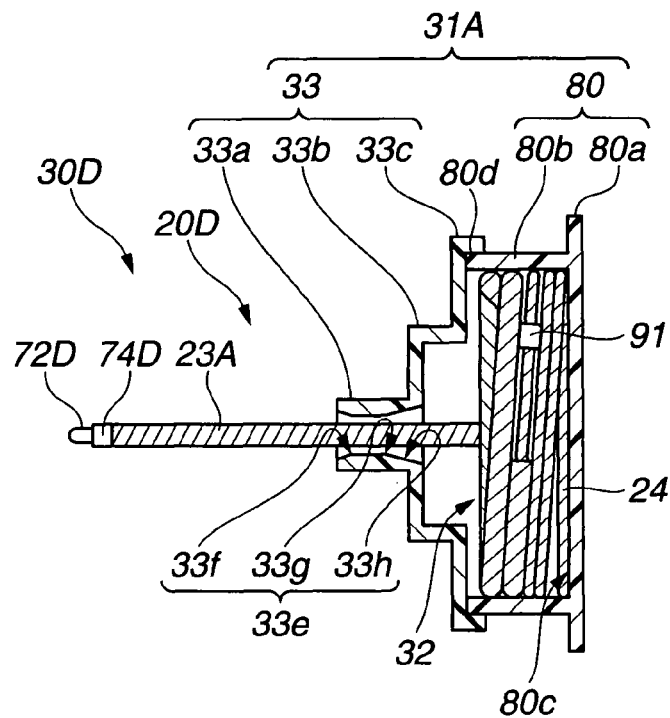
FIG. 50 is a view to illustrate the cartridge wherein a case main body in a different configuration includes a calculus fragmenting device in another configuration.
Figure 51:
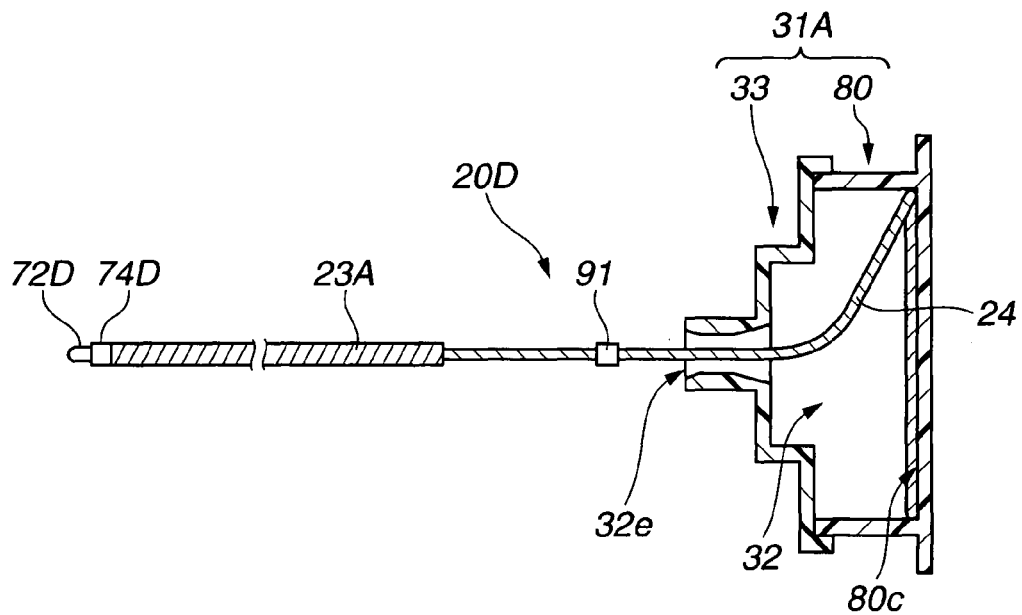
FIG. 51 is a view to illustrate a configuration of the sheath portion configured by the coil sheath and the operation wire disposed in the case main body.

As shown in FIG. 50, the operation wire 24 and the coil sheath 23A of the calculus fragmenting device 20D are housed in a rolled state in the sheath housing portion 32 of the case main body 31A described referring to FIGS. 32, 33. The proximal end side of the operation wire 24 shown in FIG. 51 is extended from the proximal end surface of the coil sheath 23A. The end portion of the operation wire is integrally fixed, with a fixing tool not shown, to a bottom surface 80c of a space configured by the plane portion 80a and the annular portion 80b configuring the second member 80.

In the present embodiment, fixed at a half-way portion of the operation wire 24 extending from the proximal end surface of the coil sheath 23A is a contact member 91 which is an advancing/retreating movement switching mechanism portion. The contact member 91 contacts the proximal end surface of the coil sheath 23A as the operation wire 24 is advanced in a distal end direction. The contact member 91 is located at a position set to be at a predetermined distance in a state where the chip 72D is located at the distal end surface of the ring member 74D. By moving the contact member 91 by the distance, the basket portion 71 is entirely protruded from the distal end surface of the ring member 74D into the expanded state shown in FIG. 49.

Other components are the same as those of the calculus fragmenting device 20B and the clip device 20C, and the same members are attached with the same reference symbols, the descriptions thereof being omitted. Note that a cartridge 30D housing the sheath portion 21 of the calculus fragmenting device 20D is to be mounted to the treatment instrument mounting portion 8b of the electric operation device 8D.

Referring to FIGS. 52 to 59, there will be described actions of the calculus fragmenting device 20D wherein the cartridge 30D configured as mentioned above is mounted to the treatment instrument mounting portion 8b of the electric operation device 8D.

In performing an operation, the staff first locates the case main body 31A at a predetermined position of the treatment instrument mounting portion 8b. The staff also mounts the spigot body 47 compatible with the coil sheath 23A to the attachment board 46 included in the inserting/pulling-out device 40, and mounts the connection tube 9, of which one end portion is connected to the treatment instrument lead-in port 12b, to the tube attaching portion 48 by the other end portion. Further, the staff electrically connects the signal cable 2a of the operation instruction device 2 to the control device 7, and also electrically connects the control device 7 and the electric operation device 8D with the signal cable 7b.

Figure 52:
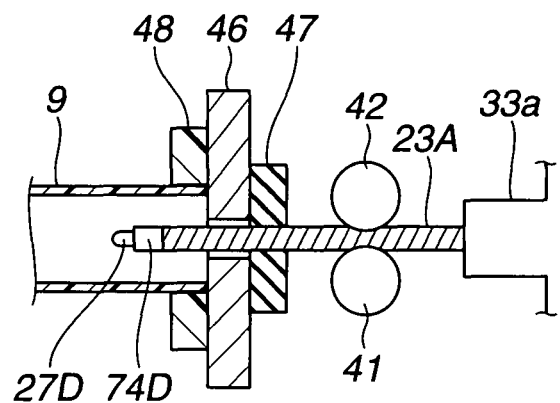
FIG. 52 is a view to illustrate a state where the coil sheath of the calculus fragmenting device is nipped by the rollers.

Next, the staff locates in the connection tube 9 the coil sheath 23A exposed from the distal end surface of the sheath lead-out portion 33a, via between the rollers 41, 42 in an opened state and through the spigot body 47, the attachment board 46, and the tube attaching portion 48. Then, the staff locates the opening/closing lever 49 as shown in the solid line to nip the coil sheath 23A between the rollers 41, 42, as shown in FIG. 52. This completes the pre-operation preparation.

Endoscopic observation is performed to confront the distal end portion 11a of the endoscope 10 with, for example, a duodenal papilla not shown. Then, in using the calculus fragmenting device 20D, the operator operates to incline the operation lever 5a of the operation instruction device 2 toward the distal end side, to lead the sheath portion 21 into, for example, a bile duct (not shown).

Figure 53:
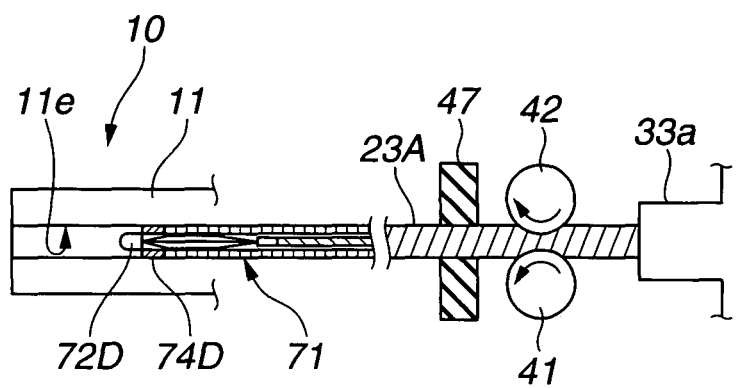
FIG. 53 is a view to illustrate a state where the coil sheath of the calculus fragmenting device is being advanced by the rollers.
Figure 54:
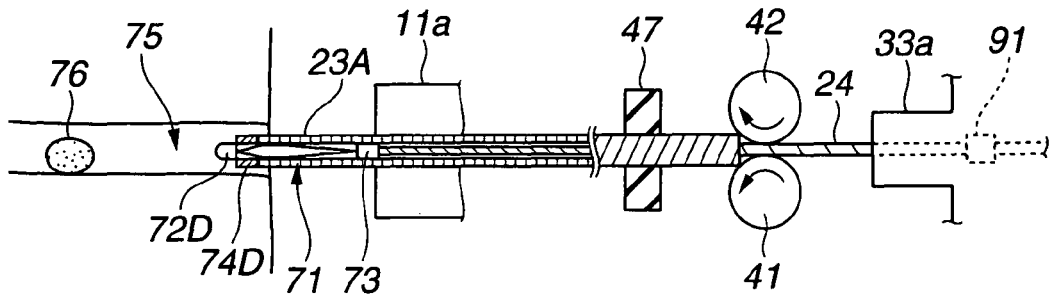
FIG. 54 is a view to illustrate a state where the operation wire, instead of the coil sheath, is nipped by the rollers

When the operator operates to incline the operation lever 5a, the first motor 43 is rotated and driven in a predetermined direction, thus starting to rotate the roller 41 as shown in an arrow in FIG. 53. As the roller 41 is rotated, the coil sheath 23A is advanced against the urging force of the spigot body 47. The coil sheath 23A passes through the treatment instrument lead-in port 12b included in the operation portion 12 of the endoscope 10, to be inserted and subsequently advanced in the treatment instrument channel 11e provided in the insertion portion 11 of the endoscope 10.

Then, the coil sheath 23A advancing in the treatment instrument channel 11e is led out from the distal end surface of the distal end portion 11a, which subsequently results in a state where the coil sheath 23A is led in the bile duct 75 by the predetermined amount. At this time, the operation wire 24, instead of the coil sheath 23A, is nipped between the rollers 41, 42.

As a result, the operation wire 24 is advanced in the coil sheath 23A as the roller 41 is rotated, protruding the fragmenting tool 70 from the coil sheath 23A, thus locating the basket portion 71 expanded in the bile duct 75.

Figure 55:
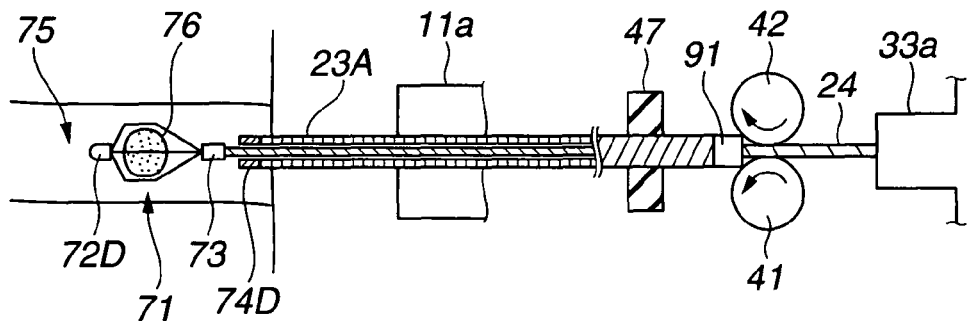
FIG. 55 is a view to illustrate a state where the operation wire is advanced by the rollers to expand a basket portion of the fragmenting tool so as to take in a calculus therein.

At this time, as shown in FIG. 55, the contact member 91 passes through between the rollers 41, 42, the distal end surface of the contact member 91 coming into contact with the proximal end surface of the coil sheath 23A, placing the proximal end surface of the coil sheath 23A apart from the rollers 41, 42 by the length of the contact member 91, which results in the rotational driving force non-transmitting state. Here, the operator stops operating the operation lever 5a.

Figure 56:
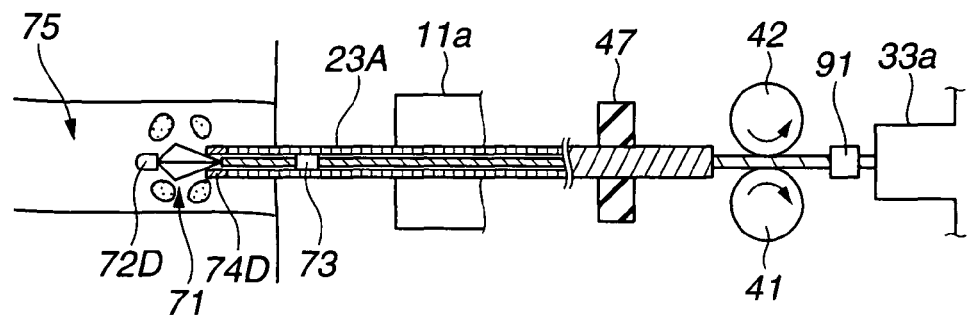
FIG. 56 is a view to illustrate a state where the calculus taken in the basket portion is fragmented by towing the operation wire by means of the rollers.

Next, the operator operates to incline the operation lever 5a toward the proximal end side to rotate and drive the first motor 43 in a direction reverse to that mentioned above, the roller 41 rotating as shown in an arrow in FIG. 56. Because the operation wire 24 is located between the rollers 41, 42 and the proximal end surface of the coil sheath 23A is apart from the rollers 41, 42, as the roller 41 is rotated, the operation wire 24 is towed, the contact member 91 then passing through between the rollers 41, 42, followed by the operation wire 24 being again retreated to be housed in the sheath housing portion 32 with the rotation of the roller 41.

Figure 57:
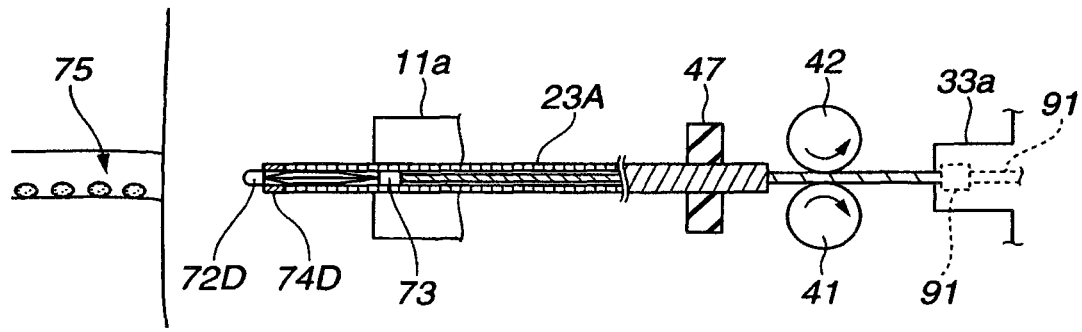
FIG. 57 is a view to illustrate a state where it is finished to fragment the calculus by towing the operation wire by means of the rollers.

With the retreat of the operation wire 24 as the roller 41 is rotated, the expanded basket portion 71 is gradually reduced in diameter as being housed in the coil sheath 23A. If, at this time, the expanded basket portion 71 includes the calculus 76 taken therein, the calculus 76 is fractured as shown in FIG. 56 by the elastic wires 71a of the basket portion 71 reducing in diameter as the operation wire 24 is retreated. Subsequently, by further continuing the retreat of the operation wire 24, the proximal end surface 72r of the chip 72D is caused to contact the distal end surface of the ring member 74D as shown in FIG. 57, therewith completing the fracturing of the calculus 76.

Figure 58:
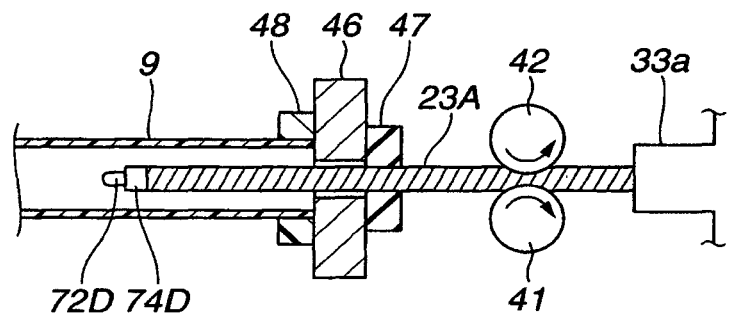
FIG. 58 is a view to illustrate a state where the coil sheath is being retreated by means of the rollers.
Figure 59:
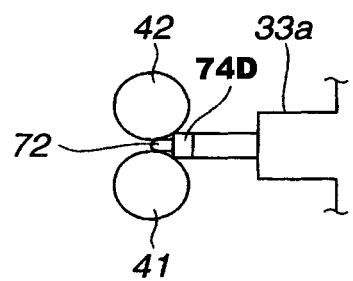
FIG. 59 is a view to illustrate a state where it is finished to pull out the sheath portion.

The contact of the proximal end surface 72r of the chip 72D with the distal end surface of the ring member 74D causes the coil sheath 23A to be integrally retreated with the operation wire 24 retreated. Subsequently, the coil sheath 23A, instead of the operation wire 24, is nipped between the rollers 41, 42, retreating the coil sheath 23A as the roller 41 rotates as shown in FIG. 58, thereby housing in the sheath housing portion 32 the coil sheath 23A in which the operation wire 24 is inserted. After the coil sheath 23A is pulled out of the treatment instrument channel 11e, passing through the connection tube 9, the ring member 74D provided at the distal end of the coil sheath 23A passes through between the rollers 41, 42 as shown in FIG. 59, therewith completing housing the operation wire 24 and the coil sheath 23A into the sheath housing portion 32. Here, the operator stops operating the operation lever 5a.

In this manner, by having the coil sheath to serve as the outer sheath, without providing the outer sheath, inserting the operation wire serving as an insertion member in the hollow portion of the coil sheath, providing the outer sheath with the ring member, and providing the chip and the contact member on the operation wire side, it is made possible to advance/retreat the coil sheath and the operation wire as needed by means of the rollers, to fracture the calculus without using the activating device.

Having described the preferred embodiments of the invention referring to the accompanying drawings, it should be understood that the present invention is not limited to those precise embodiments and various changes, and modifications thereof could be made by one skilled in the art without departing from the spirit or scope of the invention as defined in the appended claims.

What is claimed is:

1. A medical system comprising:
a treatment instrument comprising:
an exterior member having a distal end and a proximal end and a hollow portion extended in an axial direction, and an insertion member that is longer than the exterior member and is adapted to be inserted advanceably and retreatably into the hollow portion of the exterior member; and
a treating portion that is moveable in the axial direction with respect to the exterior member and disposed at a distal end side of the insertion member; and
an insertion portion inserting/pulling-out device comprising a pair of rollers adapted to press and nip at least one of the exterior member and the insertion member, and to transmit a driving force to the exterior member or the insertion member to advance or retreat at least one of the exterior member and the insertion member in the axial direction;
a driving force non-transmitting portion fixed to an outer surface of a half-way portion of the insertion member extending from a proximal end surface of the exterior member, the driving force non-transmitting portion being adapted to move from a position proximal of the pair of rollers to a position distal of the pair of rollers and in contact with the proximal end surface of the exterior member to transmit a driving force from the pair of rollers to the exterior member; and
an advancing/retreating movement switching mechanism portion adapted to advance the insertion member along with a movement of the exterior member when the exterior member is in an advancing state, and to retreat the exterior member along with a movement of the insertion member when the insertion member is in a retreating state.

2. The medical system according to claim 1, wherein the advancing/retreating movement switching mechanism portion comprises:
an engaging member fixed at a predetermined position on the outer surface on the distal end side of the insertion member; and
a stopper member configured at a predetermined position on an inner circumferential surface on a distal end side of the exterior member.

3. The medical system according to claim 1,
wherein the driving force non-transmitting portion is a contact member fixed to the outer surface of the half-way portion of the insertion member extending from the proximal end surface of the exterior member, and
wherein the contact member is adapted to come into contact with the proximal end of the exterior member to move a position of the proximal end of the exterior member by a length of the contact member.

4. The medical system according to claim 1, further comprising an exterior member holding portion proximate to the pair of rollers, wherein the exterior member holding portion is adapted to be in close contact with an outer surface of the exterior member to apply a predetermined resistance force to the exterior member.

5. The medical system according to claim 1, wherein by further advancing the insertion member from a state where the driving force non-transmitting portion is in contact with the proximal end surface of the exterior member, the exterior member is pushed by the driving force non-transmitting portion and advances, causing the pair of rollers and the exterior member to be positioned away from each other.

6. A medical system comprising:
a treatment instrument comprising:
an insertion portion comprising an exterior member configuring an exterior, the exterior member having a distal end and a proximal end and being extended in an axial direction, and an insertion member longer than the exterior member, the insertion member being advanceably and retreatably inserted into the exterior member, and
a function portion disposed at a distal end of the insertion portion;
an insertion portion inserting/pulling-out device comprising a pair of rollers adapted to press and nip an outer surface of the exterior member and the insertion member, the insertion portion inserting/pulling-out device transmitting a rotational driving force of the pair of rollers to the exterior member or the insertion member to advance and retreat the insertion portion;
a rotational driving force non-transmitting portion fixed to an outer surface of a half-way portion of the insertion member extended from a proximal end surface of the exterior member, the rotational driving force non-transmitting portion being adapted to move from a position proximal of the pair of rollers to a position distal of the pair of rollers and in contact with the proximal end surface of the exterior member to transmit a driving force from the pair of rollers to the exterior member; and
an advancing/retreating movement switching mechanism portion adapted to advance the insertion member along with a movement of the exterior member when the exterior member is in an advancing state, and to retreat the exterior member along with a movement of the insertion member when the insertion member is in a retreating state.

7. The medical system according to claim 6, wherein the advancing/retreating movement switching mechanism portion comprises:
an engaging member fixed at a predetermined position on the outer surface on the distal end side of the insertion member; and
a stopper member configured at a predetermined position on an inner circumferential surface on a distal end side of the exterior member,
wherein when the exterior member moves to advance, the stopper member and the engaging member contact each other, so that the exterior member and the insertion member integrally advance, and when the insertion member moves to retreat, the engaging member and the stopper member contact each other, so that the exterior member and the insertion member integrally retreat.

8. The medical system according to claim 6,
wherein the rotational driving force non-transmitting portion is a contact member, and
wherein the contact member is adapted to come into contact with the proximal end of the exterior member to move a position of the proximal end of the exterior member by a length of the contact member.

9. The medical system according to claim 8, wherein the contact member serves also as a moving distance setting member to set a moving distance of the function portion.

10. The medical system according to claim 6, wherein the pair of rollers are elastic resin members, and an interval between the pair of rollers is narrower than an outer diameter dimension of the insertion member.

11. The medical system according to claim 6, wherein the insertion portion inserting/pulling-out device further comprises:
- an exterior member holding portion proximate to the pair of rollers,
- wherein the exterior member holding portion is adapted to be in close contact with the outer surface of the exterior member to apply a resistance force to prevent the exterior member from advancing along with advancing of the insertion member when the insertion member is advanced by the rotational driving force of the pair of rollers.

12. The medical system according to claim 6, wherein, in a configuration in which the insertion member configuring the insertion portion is tubular and flexible, the insertion portion further comprises a small-diameter insertion member to be inserted into a hollow portion of the insertion member, the small-diameter insertion member being flexible and longer and smaller in diameter than the insertion member.

13. The medical system according to claim 6, wherein by further advancing the insertion member from a state where the driving force non-transmitting portion is in contact with the proximal end surface of the exterior member, the exterior member is pushed by the driving force non-transmitting portion and advances, causing the pair of rollers and the exterior member to be positioned away from each other.

14. The medical system according to claim 6, wherein the function portion is movable in the axial direction with respect to the exterior member.

15. An endoscope system comprising:
- an endoscope comprising a treatment instrument channel;
- a treatment instrument configured to be inserted into the treatment instrument channel of the endoscope, wherein the treatment instrument comprises:
  - an insertion portion comprising:
    - an exterior member configuring an exterior, the exterior member having a distal end and a proximal end and being extended in an axial direction, and
    - an insertion member longer than the exterior member, the insertion member being advanceably and retreatably inserted into the exterior member, and
    - a function portion disposed at a distal end of the insertion portion;
  - an insertion portion inserting/pulling-out device comprising a pair of rollers configured to press and nip an outer surface of the exterior member and the insertion member, the insertion portion inserting/pulling-out device being configured to transmit a rotational driving force of the pair of rollers to the exterior member or the insertion member to advance and retreat the insertion portion;
  - a rotational driving force non-transmitting portion fixed to an outer surface of a half-way portion of the insertion member extended from a proximal end surface of the exterior member, the rotational driving force non-transmitting portion being adapted to move from a position proximal of the pair of rollers to a position distal of the pair of rollers and in contact with the proximal end surface of the exterior member to transmit a driving force from the pair of rollers to the exterior member; and
  - an advancing/retreating movement switching mechanism portion configured to advance the insertion member along with a movement of the exterior member when the exterior member is in an advancing state, and to retreat the exterior member along with a movement of the insertion member when the insertion member is in a retreating state.

16. The endoscope system according to claim 15, wherein the advancing/retreating movement switching mechanism portion comprises:
- an engaging member to be fixed at a predetermined position on the outer surface on the distal end side of the insertion member; and
- a stopper member configured at a predetermined position on an inner circumferential surface on a distal end side of the exterior member,
- wherein when the exterior member moves to advance, the stopper member and the engaging member contact to each other, so that the exterior member and the insertion member integrally advance, and when the insertion member moves to retreat, the engaging member and the stopper member contact to each other, so that the exterior member and the insertion member integrally retreat.

17. The endoscope system according to claim 15,
- wherein the rotational driving force non-transmitting portion is a contact member, and
- wherein the contact member coming into contact with the proximal end of the exterior member to move a position of the proximal end of the exterior member by a length of the contact member.

18. The endoscope system according to claim 17, wherein the contact member serves also as a moving distance setting member to set a moving distance of the function portion.

19. The endoscope system according to claim 15, wherein the air of rollers are elastic resin members, and an interval between the pair of rollers is narrower than an outer diameter dimension of the insertion member.

20. The endoscope system according to claim 15, wherein the insertion portion inserting/pulling-out device further comprises:
- an exterior member holding portion proximate to the pair of rollers,
- wherein the exterior member holding portion is adapted to be in close contact with the outer surface of the exterior member to apply a resistance force to prevent the exterior member from advancing along with advancing of the insertion member when the insertion member is advanced by the rotational driving force of the pair of rollers.

21. The endoscope system according to claim 15, wherein, in a configuration in which the insertion member configuring the insertion portion is tubular and flexible, the insertion portion further comprises a small-diameter insertion member to be inserted into a hollow portion of the insertion member, the small-diameter insertion member being flexible and longer and smaller in diameter than the insertion member.

22. The medical system according to claim 15, wherein by further advancing the insertion member from a state where the driving force non-transmitting portion is in contact with the proximal end surface of the exterior member, the exterior member is pushed by the driving force non-transmitting portion and advances, causing the pair of rollers and the exterior member to be positioned away from each other.

23. The endoscope system according to claim 15, wherein the function portion is movable in the axial direction with respect to the exterior member.

* * * * *